United States Patent
Kaya et al.

(10) Patent No.: US 9,315,558 B2
(45) Date of Patent: Apr. 19, 2016

(54) USE OF INTERLEUKIN 10 MRNA TRANSFECTED MACROPHAGES IN ANTI-INFLAMMATORY THERAPIES

(75) Inventors: Ziya Kaya, Heidelberg (DE); Hugo Katus, Heidelberg (DE); Oliver Zimmermann, Waltenhofen (DE); Wolfgang Rottbauer, Ulm (DE); Jan Torzewski, Immenstadt (DE)

(73) Assignees: RUPRECHT-KARLS-UNIVERSITÄT HEIDELBERG, Heidelberg (DE); UNIVERSITÄT ULM, Ulm (DE)

( * ) Notice: Subject to any disclaimer, the term of this patent is extended or adjusted under 35 U.S.C. 154(b) by 7 days.

(21) Appl. No.: 13/884,888

(22) PCT Filed: Nov. 14, 2011

(86) PCT No.: PCT/EP2011/070027
§ 371 (c)(1),
(2), (4) Date: Jul. 30, 2013

(87) PCT Pub. No.: WO2012/062930
PCT Pub. Date: May 18, 2012

(65) Prior Publication Data
US 2013/0303596 A1 Nov. 14, 2013

(30) Foreign Application Priority Data

Nov. 12, 2010 (EP) .................................. 10190950

(51) Int. Cl.
| | | |
|---|---|---|
| C12N 5/00 | (2006.01) | |
| C12N 5/071 | (2010.01) | |
| C07K 14/54 | (2006.01) | |
| A61K 38/20 | (2006.01) | |
| C12N 5/0786 | (2010.01) | |
| A61K 35/15 | (2015.01) | |

(52) U.S. Cl.
CPC .............. C07K 14/5428 (2013.01); A61K 35/15 (2013.01); A61K 38/2066 (2013.01); C12N 5/0645 (2013.01)

(58) Field of Classification Search
CPC .................................................. A61K 38/2066
USPC .......................................... 435/325, 366, 372
See application file for complete search history.

(56) References Cited

U.S. PATENT DOCUMENTS

| | | | |
|---|---|---|---|
| 6,384,202 B1 | 5/2002 | Sedlacek et al. | |
| 2011/0104127 A1 | 5/2011 | Torzewski et al. | |

FOREIGN PATENT DOCUMENTS

| | | |
|---|---|---|
| WO | WO 93/19770 | 10/1993 |
| WO | WO 96/06941 | 3/1996 |
| WO | WO 2007/090647 A1 | 8/2007 |

OTHER PUBLICATIONS

Van Strien et al., (May 2010, Gene Therapy, vol. 17(5), pp. 662-671).*
Akiyama et al. (2000, Neurobiology of Aging, vol. 21, pp. 383-421).*
Hirsch et al. (2012, Parkinsonism and Related Disorders, vol. 18S1, pp. S210-S212).*
Wilson et al. (2002, Molecular Therapy, vol. 6(6), pp. 710-717).*
Zhang et al. (2009, Methods Mol. Biol., vol. 531, pp. 1-18).*
Feterowski et al. (2004. Eur. J. Immunol., vol. 34, pp. 3664-3673).*
International Search Report and Written Opinion issued in related International Patent Application No. PCT/EP2011/070027, dated Dec. 29, 2011.
Bendayan, et al., "Giant Cell Myocarditis and Heart Transplantation," *J. Heart Lung Transplant*, vol. 27, pp. 698-699 (2008).
Cihakova et al., "Pathogenesis of myocarditis and dilated cardiomyopathy," *Adv. Immunol.*, vol. 99, pp. 95-114 (2008)[Abstract Only].
Dec et al., "Idiopathic Dilated Cardiomyopathy," *The New England Journ. of Med.*, vol. 331, p. 1564 (1994).
Deighton et al., "Management of Rheumatoid Arthritis: Summary of NICE Guidance," *BMJ*, vol. 338, pp. 710-715 (2009).
El-Shemi et al., "Suppression of experimental crescentic glomerulonephritis by interleukin-10 gene transfer," *Kidney Intern.*, vol. 65, pp. 1280-1289 (2004).
Fautrel, "Choice of Second-Line Disease-Modifying Antirheumatic Drugs After Failure of Methotrexate Therapy for Rheumatoid Arthritis: A Decision Tree for Clinical Practice Based on Rheumatologists' Preferences," *Arthritis Rheum*, vol. 61, No. 4, pp. 425-434 (2009).
Fuse et al., "Short-term prognostic value of initial serum levels of interleukin-10 in patients with acute myocarditis," *The Europ. Journ. of Heart Failure*, vol. 7, pp. 109-112 (2005).

(Continued)

*Primary Examiner* — Anoop Singh
*Assistant Examiner* — David A Montanari
(74) *Attorney, Agent, or Firm* — Foley & Lardner LLP

(57) ABSTRACT

The present invention relates to the field of cell-based therapeutics. Specifically, the invention is concerned with a composition comprising a macrophage overexpressing interleukin 10 (IL-10) from transfected IL-10 encoding mRNA for use as a medicament. Moreover, a method for manufacturing a medicament for treating and/or preventing inflammation or a disease or disorder associated therewith comprising the steps of obtaining a macrophage from a sample of said subject, transfecting mRNA encoding IL-10 into said macrophage, and formulating said macrophage in a composition suitable for administration to the said subject, whereby the medicament is manufactured. Finally, a kit is provided for manufacturing such a medicament.

7 Claims, 20 Drawing Sheets

(56) References Cited

OTHER PUBLICATIONS

Figure 1B:
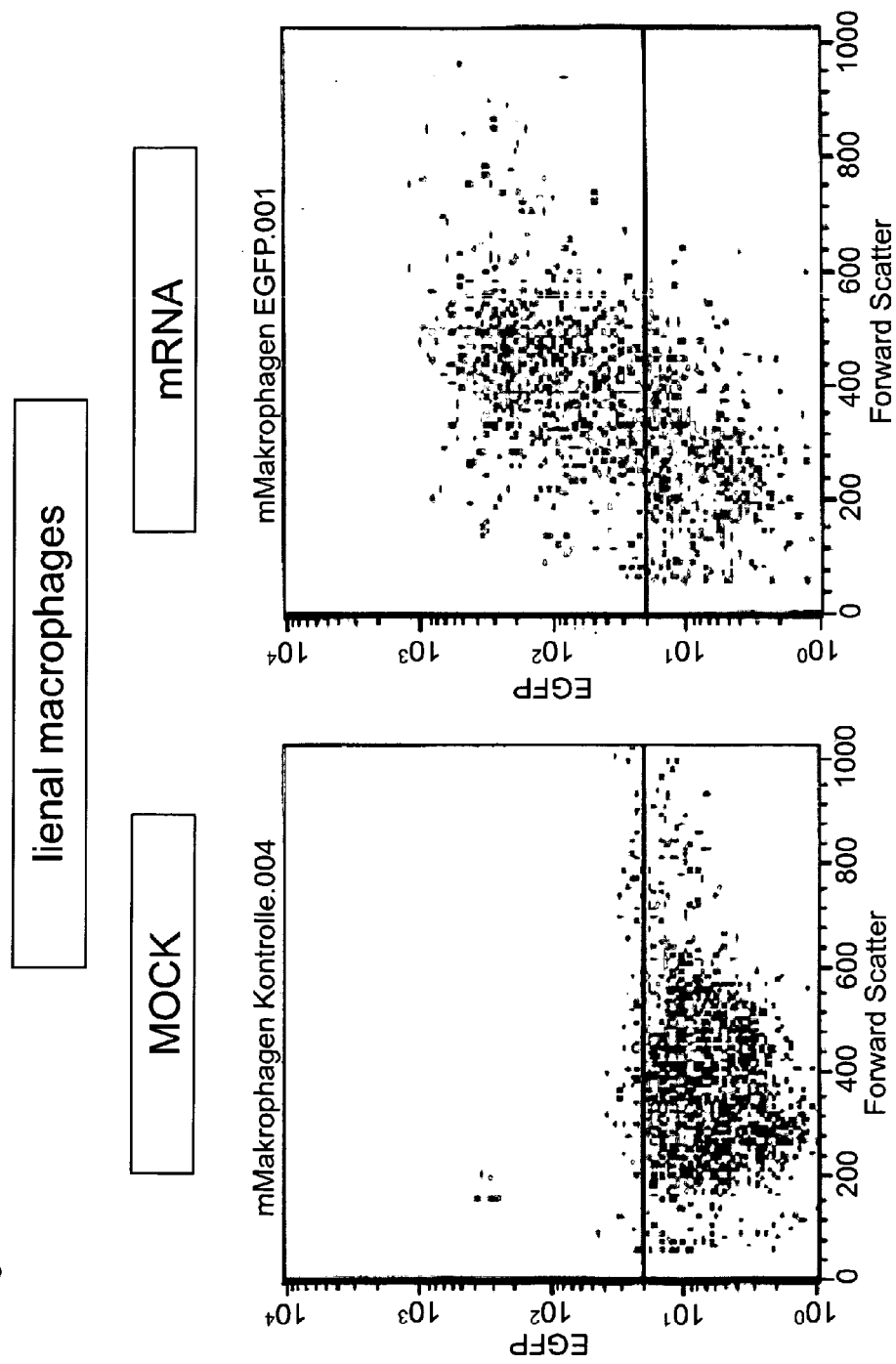

Grutz et al., "New Insights into the molecular mechanisms of interleukin-10-mediated immunosuppression," *Journ. of Leukoeyte Biology*, vol. 77, pp. 3-15 (2005).
Gupta et al., "Fulminant Myocarditis," *Nat. clin. Pract. Cardiovasc. Med.*, vol. 5, pp. 693-706 (2008).
Han et al., "Interleukin-10 overexpression in macrophages suppresses atherosclerosis in hyperlipidemic mice," *FASEB Journ.*, vol. 24, No. 8, pp. 2869-2880 (2010).
Ho et al.,, "Efficacy and Complications of Adalimumab Treatment for Medically-Refractory Chrohn's Disease: Analysis of Nationwide Experience in Scotland ," *Aliment Pharmacol. Ther.*, vol. 29, pp. 527-534 (2009).
Hunt et al., "Focused Update Incorporat4ed Into the ACC/AHA 2005 Guidelines for the Diagnosis and Management of Heart Failure in Adults," *Circulation*, vol. 119, pp. 391-479 (2009).
Kawai et al., "From Myocarditis to Cardiomyopathy: Mechanisms of Inflammation and Cell Death: Learning from the Past for the Future," *Circulation*, vol. 99, pp. 1091-1100 (1999).
Kuhl et al., "High Prevalence of Viral Genomes and Multiple Viral Infections in the Myocardium of Adults with "Idiopathic" Left Ventricular Dysfunction," *Circulation*, vol. 111, pp. 887-893 (2005).
Kuhl et al., "Interferon-β Treatment Eliminates Cardiotropic Viruses and Improves Left Ventricular Function in Patients with Myocardial Persistence of Viral Genomes and Left Ventricular Dysfunction," vol. 107, pp. 2793-2798 (2003).
Maruyama et al., "Fenofibrate, a Peroxisome Proliferator-Activated Receptor α Activator, Suppresses Experimental Autoimmune Myocarditis by Stimulating the Interleukin-10 Pathway in Rats," *J. Atheroscler Thromb.*, vol. 9, pp. 87-92 (2002).
Mason et al., "A Clinical Trail of Immunosuppressive Therapy for Myocarditis," vol. 333, No. 5, pp. 269-275 (1995).
Matsumori et al., "Effects of Free Immunoglobulin Light Chains on Viral Myocarditis," *Circ. Res.*, vol. 106, pp. 1533-1540 (2010).
McKenna et al., "Idiopathic dilated cardiomyopathy: familial prevalence and HLA distribution," *Heart*, vol. 77, pp. 549-552 (1997).
Milenkovic et al., "Quercetin Ameliorates Experimental Autoimmune Myocarditis in Rats," *J. Pharm. Pharmaceut Sci.*, vol. 13, No. 3, pp. 311-319 (2010).
Mimori, Nippon Naika Gakkai Zasshi, vol. 97, pp. 2393-2398 (2008).
Mosser et al., "Interleukin-10: new perspectives on an old cytokine," *Immunol. Rev.*, vol. 226, pp. 205-218 (2008).
Nishii et al., "Serum Levels of Interleukin-10 on Admission as a Prognostic Predictor of Human Fulminant Myocarditis," *Journ. of American College of Cardiology*, vol. 44, No. 6, pp. 1292-1297 (2004).

Nishio et al., "Treatment of Experimental Viral Myocarditis with Interleukin-10," *Circulation*, vol. 100, pp. 1102-1108 (1999).
Palaniyandi et al., "Inhibition of mast cells by interleukin-10 gene transfer contributes to protection against acute myocarditis in rats," *Eur. J. Immunol.*, vol. 34, pp. 3508-3515 (2004).
Pinderski et al., "Overexpression of Interleukin-10 by Activated T Lymphocytes Inhibits Atherosclerosis in LDL Receptor-Deficient Mice by Altering Lymphocyte and Macrophage Phenotypes," *Cir. Res.*, vol. 90, pp. 1064-1071 (2002).
Schultheiss et al., "Late-Breaking Clinical Trial Abstracts," *Circulation*, vol. 118, pp. 2309-2317. (2008).
Senolt, "Prospective new biological therapies for rheumatoid arthritis," *Autoimmun.* Rev. 9, 22 pages (2009).
Snowden, "Stem Cell Transplantation in Rheumatoid Arthritis," *Autoimmunity*, vol. 41, No. 8, pp. 625-631 (2008).
Spight et al., "Immunoregulatory effects of regulated, lung-targeted expression of IL-10 in vivo," *Am. J. Physiol. Lung Cell Mol. Physiol.*, vol. 288, pp. 251-265 (2005).
Thümmler, et al., "Cellular Therapy in Autoimmune Disease," *Z. Rheumatol.*, vol. 68, pp. 337-339 (2009) [Abstract provided].
Vandenbark et al., "Therapeutic vaccination with a trivalent T-cell receptor (TCR) peptide vaccine restores deficient FoxP3 expression and TCR Recognition in subjects with multiple sclerosis," *Immun.*, vol. 123, pp. 66-78 (2008).
Watanabe et al., "Protection Against Autoimmune Myocarditis by Gene Transfer of Interleukin-10 by Electroporation," *Circulation*, vol. 104, pp. 1098-1100 (2001).
Weil et al., "Mesenchymal stem cells attenuate myocardial functional depression and reduce systemic and myocardial inflammation during endotoxemia, " vol. 148, pp. 444-452 (2010).
Wiehe et al., "Efficient Transient Genetic Labeling of Human CD34+ Progenitor Cells for in vivo Application," *Regen. Med*, vol. 1, pp. 223-234 (2006).
Wiehe et al., "mRNA-mediated gene delivery into human progenitor cells promotes highly efficient protein expression," *J. Cell. Mol. Med.*, vol. 11, No. 3, pp. 521-530 (2007).
Zhang et al., "Effects of Methotrexate on Plasma cytokines and Cardiac Remodeling and Function in Postmyocarditis Rats," *Mediators Inflamm.*, vol. 2009, 9 pages (2009).
Zimmerman et al., Interferon B-1b Therapy in Chronic Viral Dilated Cardiomyopathy—Is There a Role for Specific Therapy? *Journ. of Cardiac Failure*, vol. 16, No. 4, pp. 348-356 (2010).
Strien et al., "Anti-inflammatory effect by lentiviral-mediated overexpression of IL-10 or IL-1 receptor antagonist in rat glial cells and macrophages," *Gene Therapy*, vol. 17, pp. 662-671 (2010).
International Preliminary Report on Patentability issued in related International Patent Application No. PCT/EP2011/070027, dated May 23, 2013.

\* cited by examiner

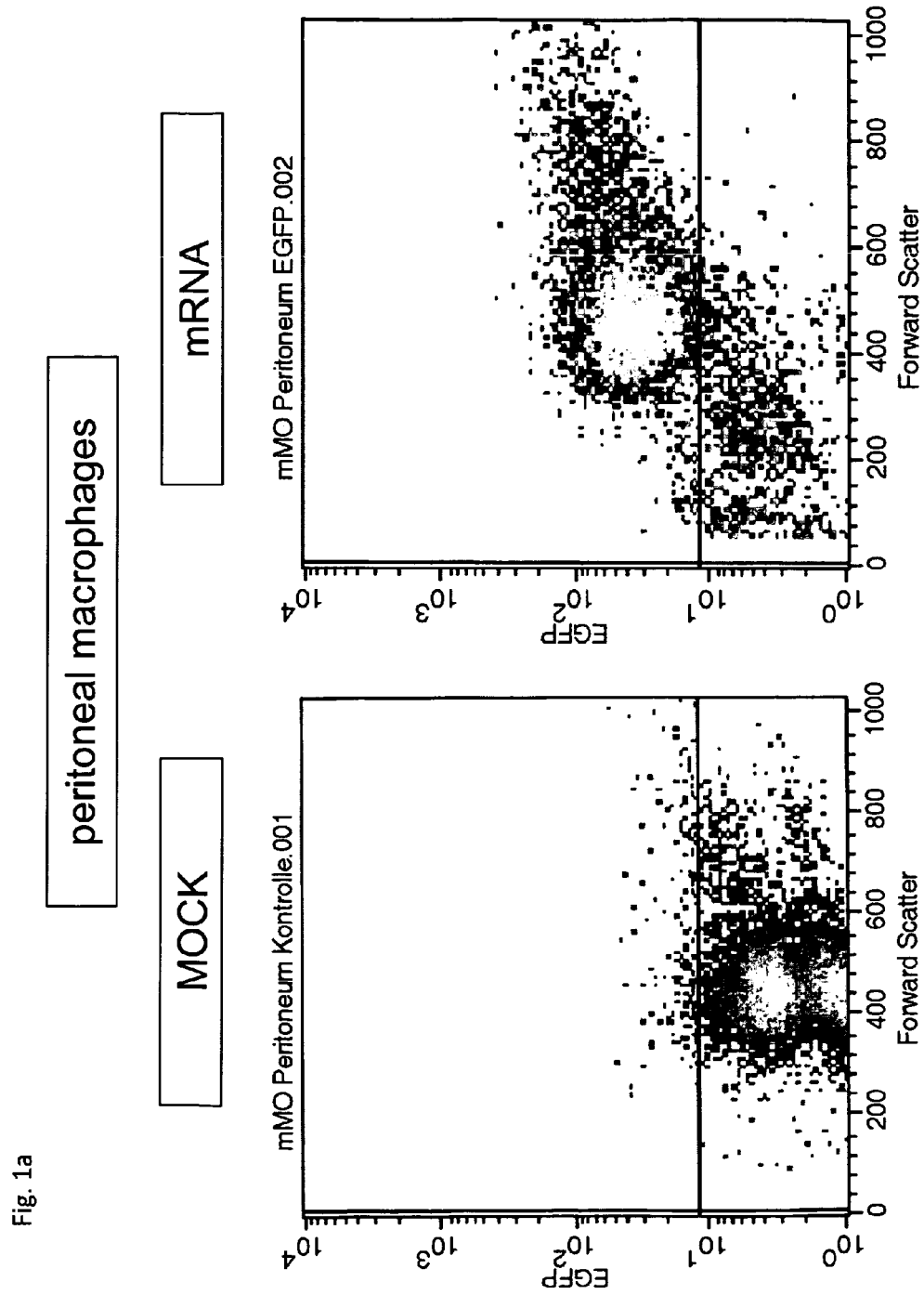

Figure 4A:
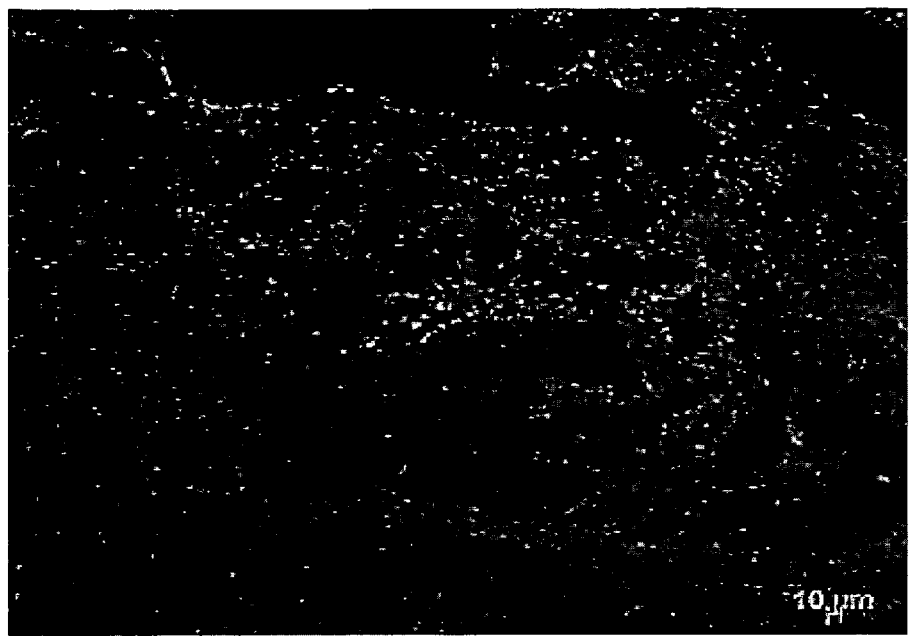
Figure 4A:
Figure 4B:
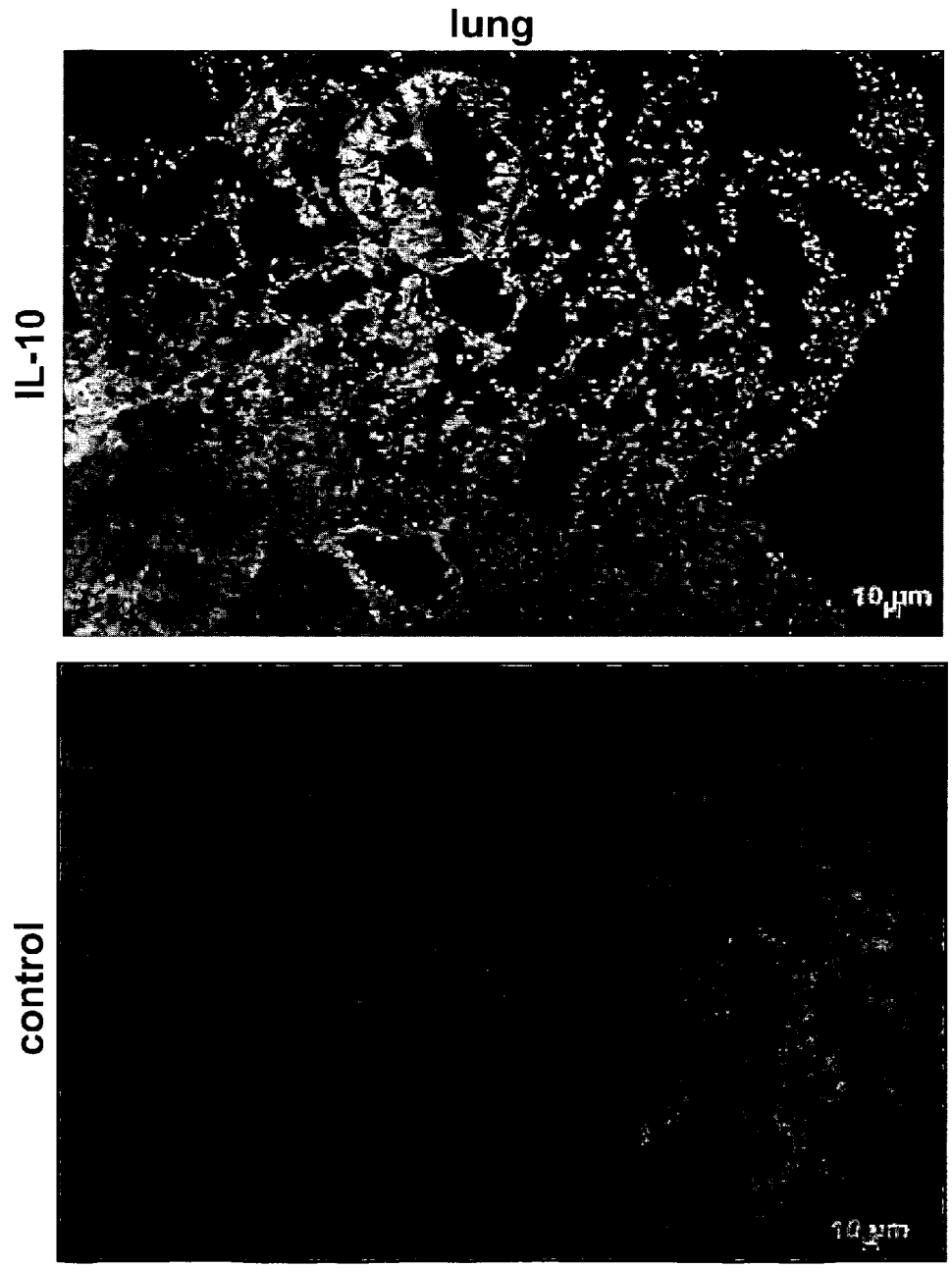
Figure 4D:
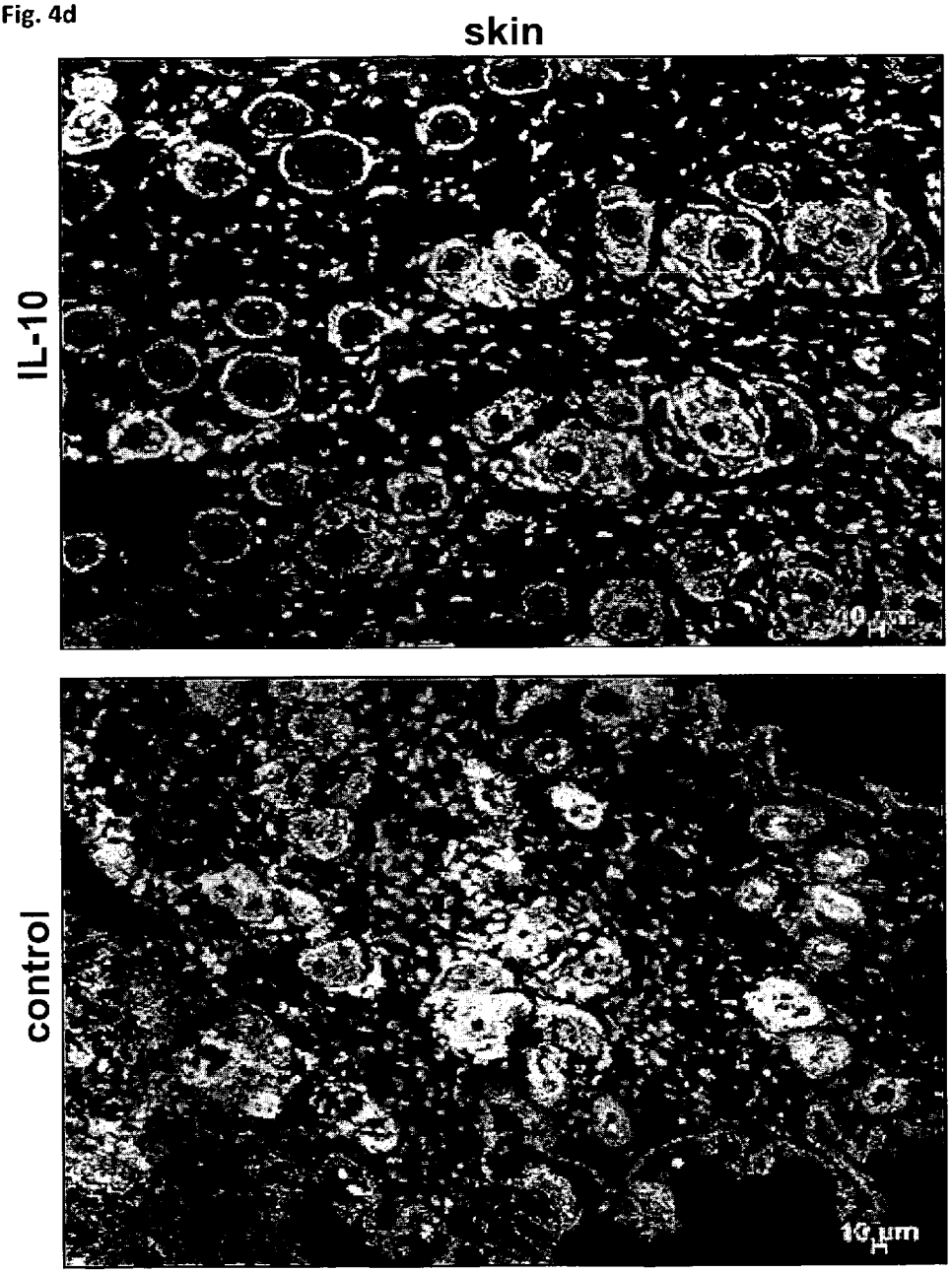
Figure 4E:
Figure 4E:
Figure 4F:
Figure 4F:
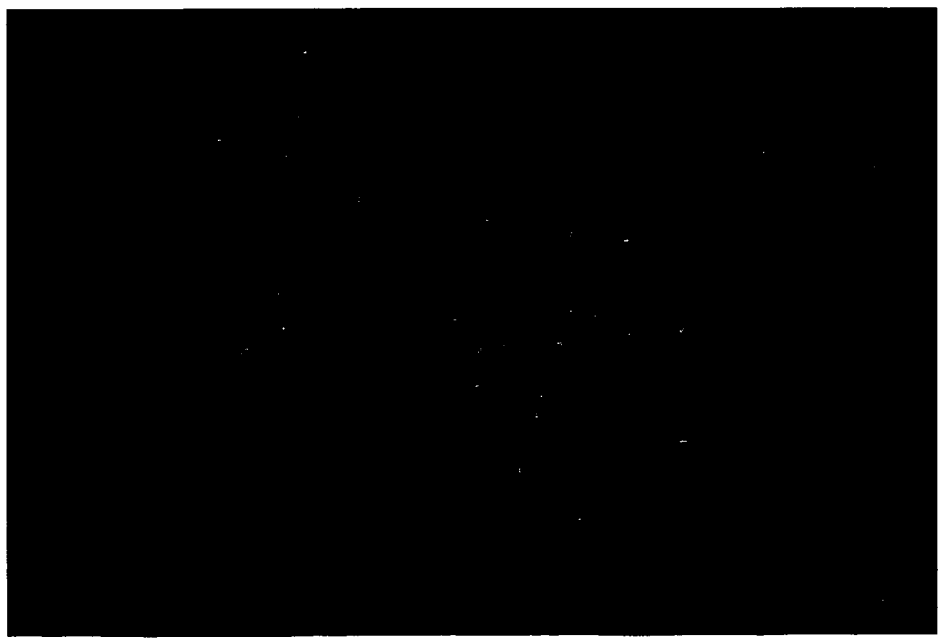
Figure 4H:
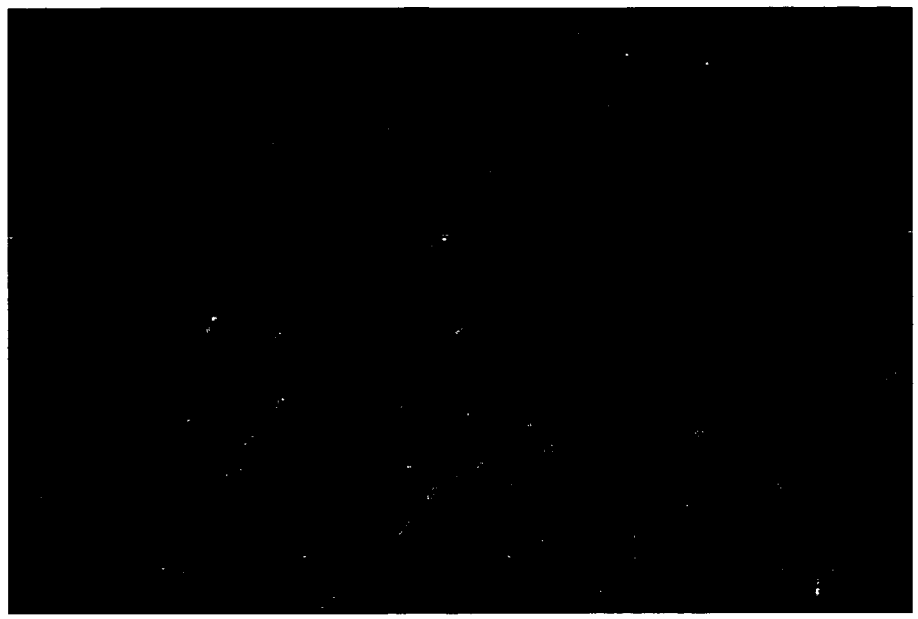
Figure 4H:
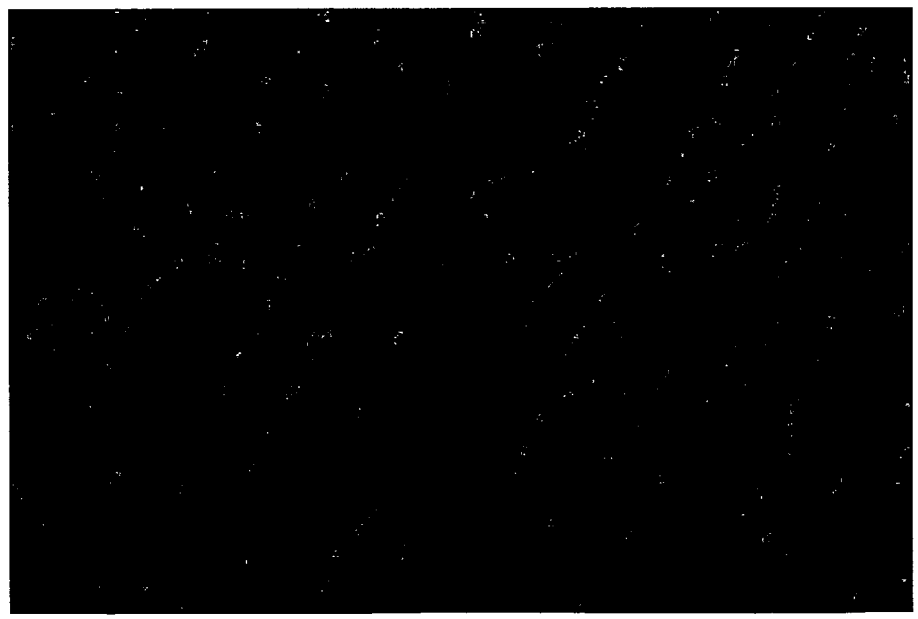

Fig. 4c   kidney
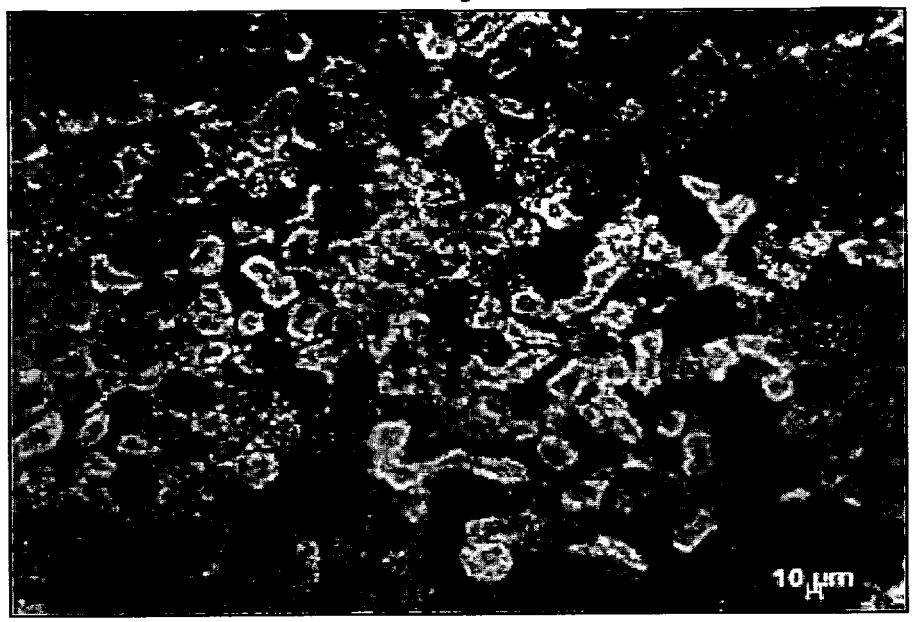
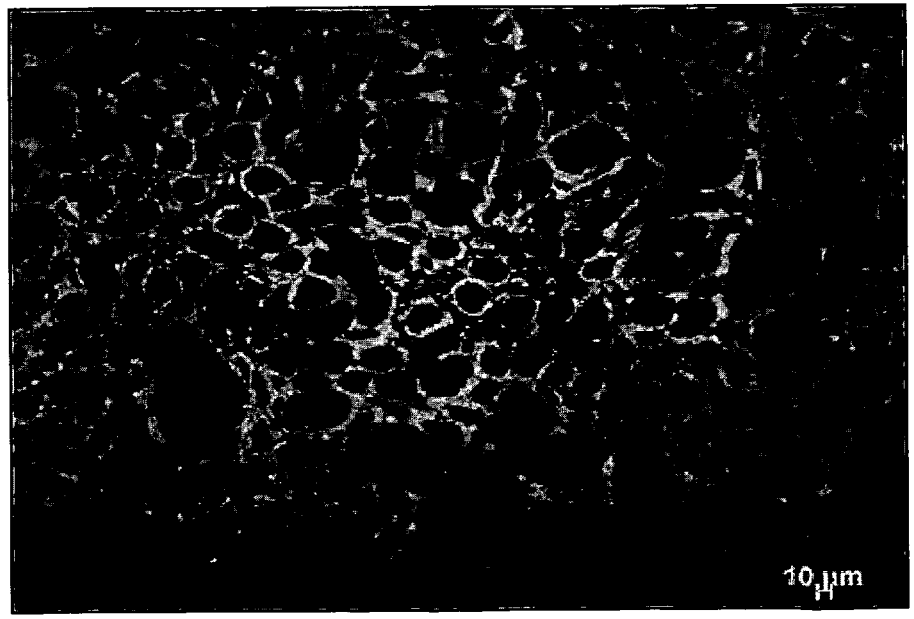

liver

IL-10 control spleen

IL-10 control

Fig. 4g      lymph node
IL-10
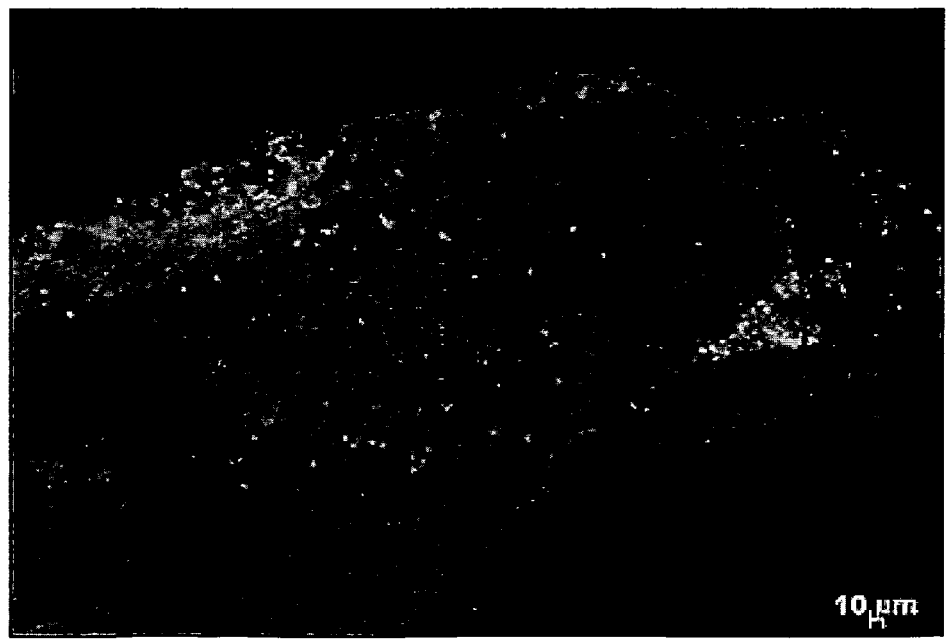
control muscle

IL-10 control

Splenocytes

Serum

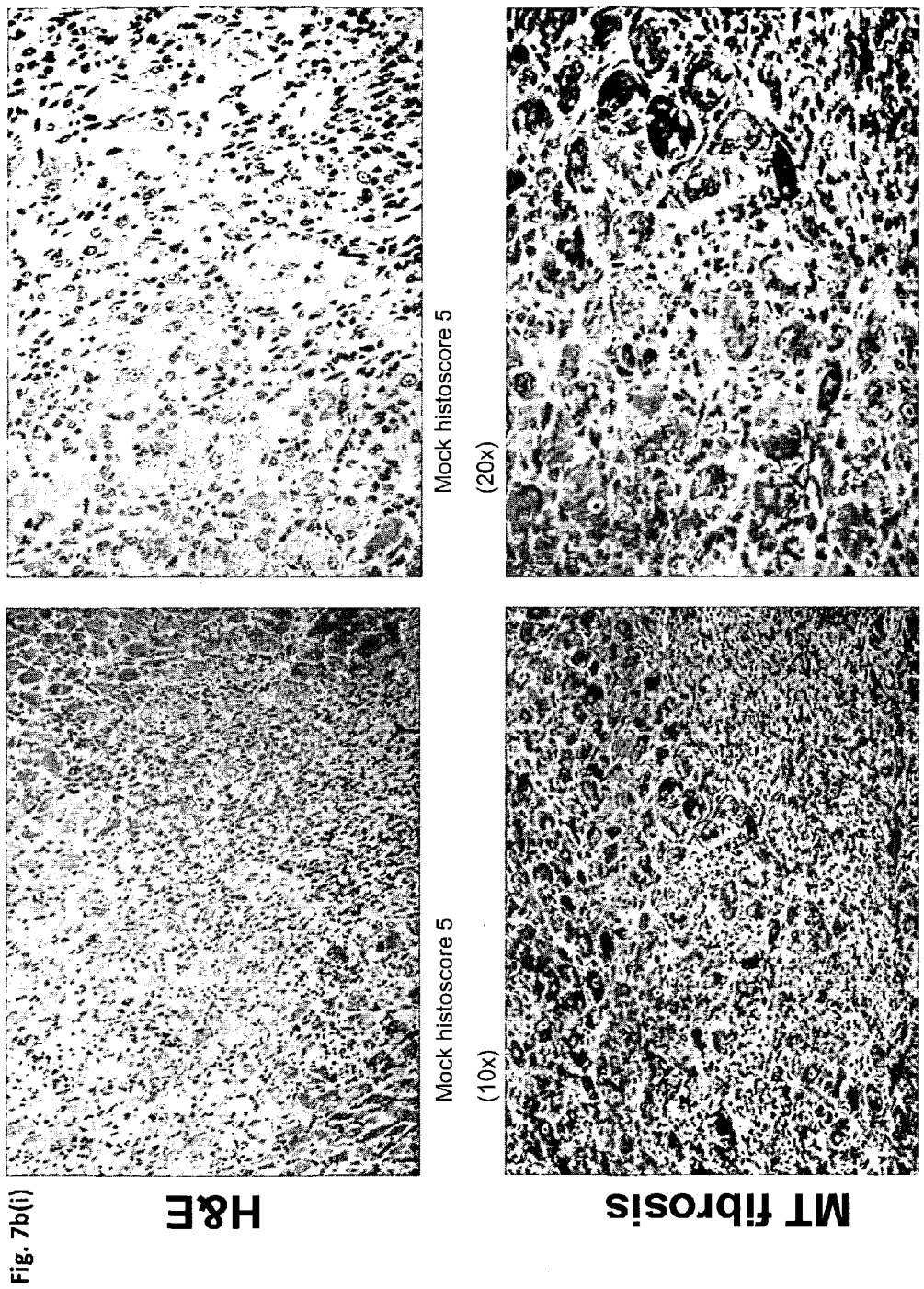

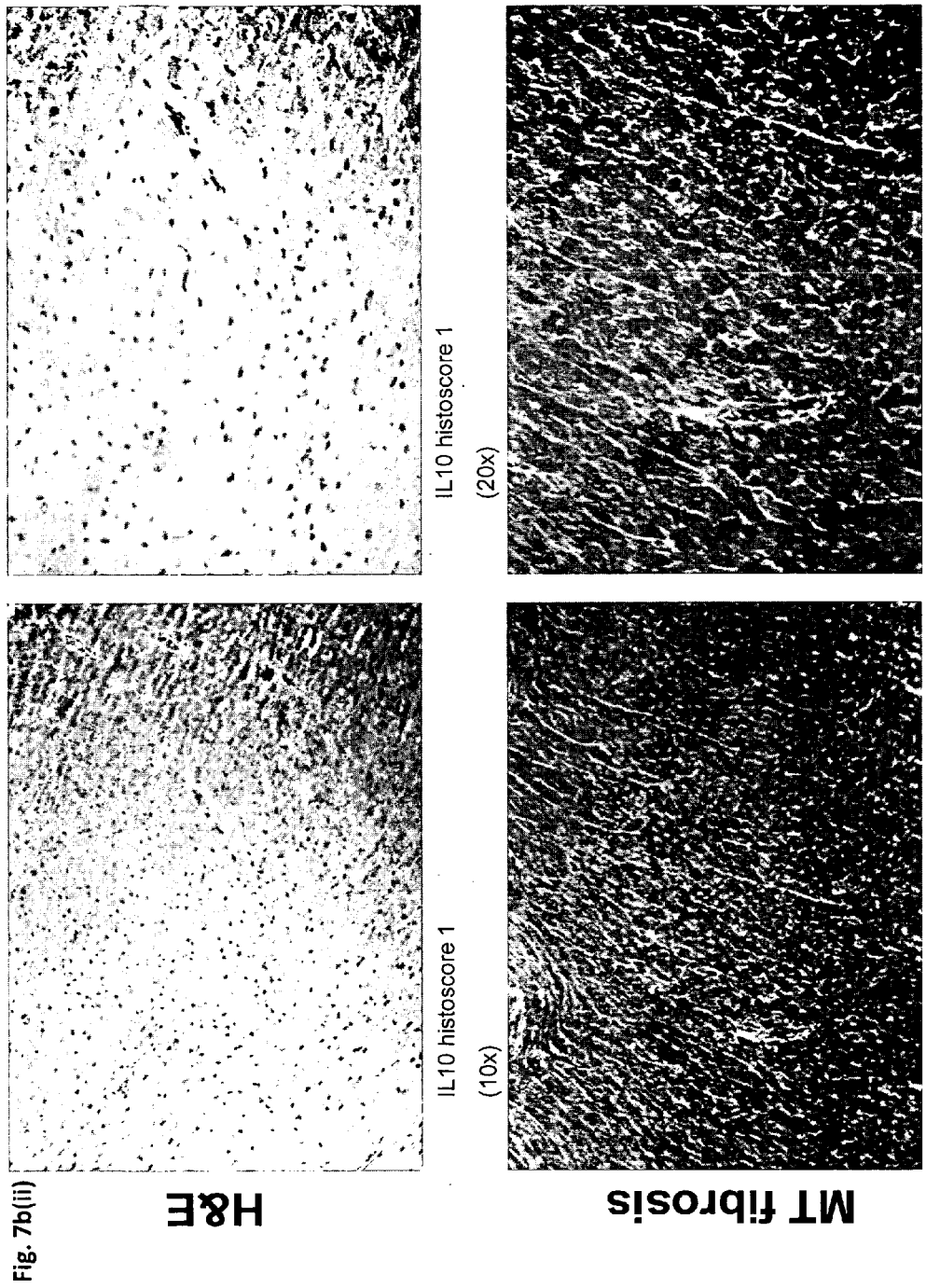

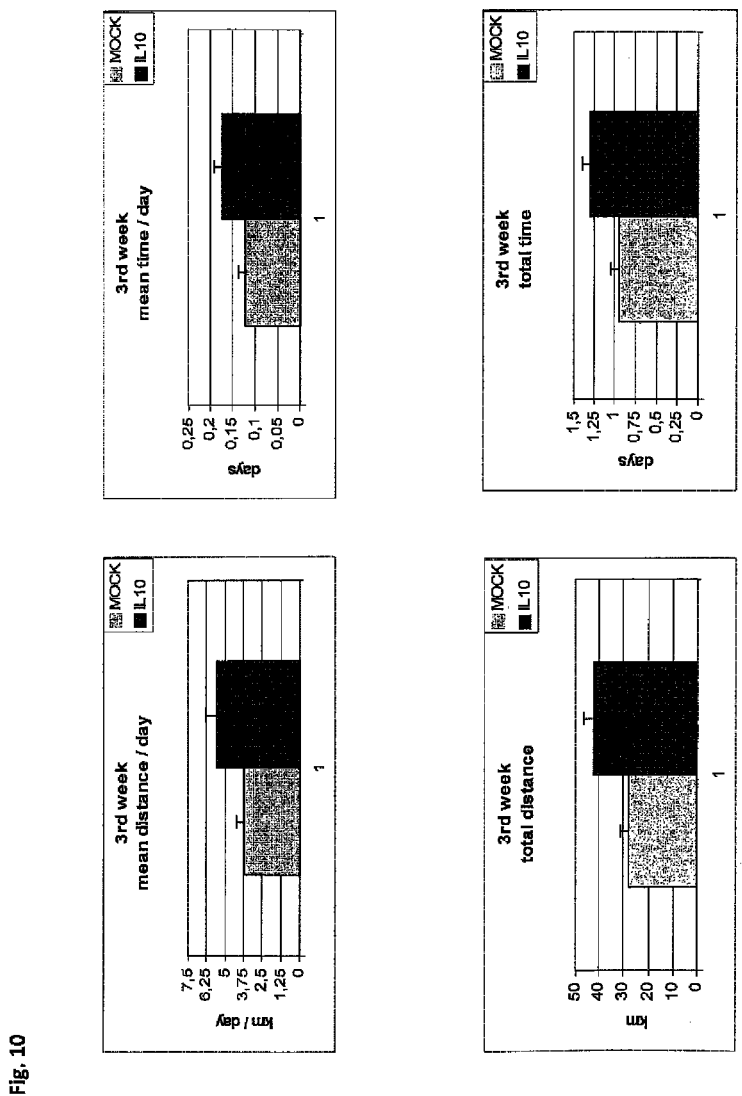

USE OF INTERLEUKIN 10 MRNA TRANSFECTED MACROPHAGES IN ANTI-INFLAMMATORY THERAPIES

This application is a National Phase of International Patent Application No. PCT/EP2011/070027, filed Nov. 14, 2011, which claims priority to European Patent Application No. 10190950.5, filed Nov. 12, 2010. The contents of these applications is incorporated herein by reference in their entirety.

The present invention relates to the field of cell-based therapeutics. Specifically, the invention is concerned with a composition comprising a macrophage overexpressing interleukin 10 (IL-10) from transfected IL-10 encoding mRNA for use as a medicament. Moreover, a method for manufacturing a medicament for treating and/or preventing inflammation or a disease or disorder associated therewith comprising the steps of obtaining a macrophage from a sample of said subject, transfecting mRNA encoding IL-10 into said macrophage, and formulating said macrophage in a composition suitable for administration to the said subject, whereby the medicament is manufactured. Finally, a kit is provided for manufacturing such a medicament.

Inflammatory reactions represent a challenge for the treatment of various diseases and disorders with accompanying inflammation. Such diseases and disorders include e.g. rheumatoid diseases such as rheumatoid arthritis or autoimmune diseases. Moreover, cardiac disease such as myocarditis are also accompanied by inflammatory reactions (Deighton 2009, BMJ 338: b702; Mimori 2008, Nippon Naika Gakki Zasshi 97: 2393-2398).

Immunosuppressive therapies are usually based on steroidal and non-steroidal antiphlogistics and, in more advanced stages, chemotherapeutics, antibodies such as Infliximab or, in particular severe cases, stem cell therapies. The current immunosuppressive therapies are unspecific and, thus, affect healthy cells and tissues as well (Senolt 2009, Autoimmun Rev 9: 102-107; Fautrel 2009, Arthritis Rheum 61: 425-434; Snowden 2008, Autoimmunity 41: 625-631; Ho 2009, Aliment Pharmacol Ther 29: 527-534). Adverse side effects of e.g. steroid-based immunosuppressive therapies are metabolic syndrome, diabetes or osteoporosis. A local or specific therapeutic approach may avoid at least some of the aforementioned drawbacks.

Myocarditis is determined by various factors and is most often a cause of cardiac diseases in young adults (Gupta 2008, Nat Clin Pract Cardiovasc Med 5: 693-706). Although acute myocarditis is often entirely cured within several weeks, some cases become chronic and may cause even more severe diseases such as dilatative cardiomyopathy and chronic heart failure. The latter disorder is notwithstanding modern therapeutic intensive care associated with a high risk of mortality and morbidity (Bendayan 2008, J Heart Lung Transplant 27: 698-699; Dec. 1, 1994, N Engl Med 331: 1564; Kawai 1999, Circulation 99: 1091-1100; Cihakova 2008, Adv Immunol 99: 96-114; Hunt 2009, Circulation 119: 391-479). Recently, inflammatory processes and viral infections have been discussed as a cause of myocarditis (McKenna 1997 Heart 77:549-552; Kühl 2005, Circulation 111: 887-893).

Interleukin 10 (IL-10) has been known for a long time as an anti-inflammatory cytokine. It represses the antigen presentation and the T-cell activation. Moreover, IL-10 inhibits the production of TH1 cytokines and promotes B-cell survival, proliferation and antibody production. It has been applied already in several therapeutic approaches (Mosser 2008 Immunol Rev 226: 205-218; Grütz 2005, Journal Leukocyte Biol 5: 3-15; Thümmler 2009, Z Rheumatol 68: 337-339; Vandenbark 2008, Immunology 123: 66-78). Moreover, IL-10 has also been used in gene therapy or cell therapeutic approaches. However, due to the use of viral vectors those approaches were less efficient and accompanied by severe side effects (El-Shemi 2004, Kidney Int 65: 1280-1289; Spight 2005, Am J Physiol Lung Cell Mol Physiol 288: 251-265; Pinderski 2002, Circ Res 90: 1064-1071). mRNA transfection of adult progenitor cells has been reported to be less harmful and applicable for human therapy (WO 2007/090647).

Thus, there is a need for an improved cell-based therapy for inflammatory disease which avoids the aforementioned drawbacks.

The technical problem underlying the present invention can be seen as the provision of means and methods for complying with the aforementioned needs. The technical problem is solved by the embodiments characterized in the claims and herein below.

Accordingly, the invention relates to a composition comprising a macrophage overexpressing interleukin 10 (IL-10) from transfected IL-10 encoding mRNA for use as a medicament.

As shown in the following examples, in vitro overexpression of IL-10 in macrophages resulted in a 7-fold increased IL-10 production. In vivo by trend higher levels of IL-10 and less inflammation was detected within the myocardium of treated compared with control mice. Mice treated with IL-10 overexpressing macrophages presented a significantly better performance in running wheel tests. Echocardiography revealed a trend towards an improved cardiac function in treated mice.

Accordingly, overexpression of IL-10 in macrophages could reduce inflammation and improve cardiac performance in a murine model of myocarditis. The use of genetically modified macrophages can thus facilitate a targeted therapy of local inflammatory processes. As the nucleofection technique is basically GMP-adapted an in vivo use in humans seems principally possible. Finally, the results shown in the following examples strongly suggest that the therapeutic approach of the present invention can be transferred to other inflammatory diseases characterized by local inflammation such as Crohn's disease, vasculitis, rheumatoid arthritis autoimmune diseases, rheumatoid disease, or multiple sclerosis.

The term "macrophage" as used herein refers to a white blood cell which is usually present in various body tissues or body fluids. They are usually mobile cells which migrate by amoeboid movements. Macrophages are formed by differentiation of monocytes. Said monocytes and macrophages are phagocytes which are involved in innate immunity as well as adaptive immunity of vertebrate animals. Macrophages have a pivotal function in phagocytosis of cellular debris and pathogens, and to stimulate lymphocytes and other immune cells to respond to a pathogen by an inflammatory reaction.

Macrophages as referred to herein are, preferably, identified by specific expression of marker proteins. A macrophage according to the present invention can be identified by at least one of the following marker proteins: CD14, CD11b, F4/80 (mice)/EMR1 (human), lysozyme M, MAC-1/MAC-3 and CD68. More preferably, the macrophage according to the present invention can be identified and/or isolated by CD11b and/or CD68. Viable macrophages can be isolated from a sample by cell separation techniques such as flow cytometry, magnetic bead-based affinity purification techniques or affinity chromatography using antibodies or aptamers which specifically recognize the aforementioned marker proteins and, in particular, CD11b.

Macrophages can be isolated from various different body tissues and body fluids of a subject including blood, lymph, liquor, saliva, and others. More preferably, the macrophage according to the present invention can be isolated from a body tissue such as spleen or peritoneal tissue and, most preferably, from the peritoneal tissues. Preferably, a subject according as meant in this specification is a mammal. Preferably, said mammal is a rodent, such as a mouse or a rat, a pet, such as a cat or dog, or a farming animal such as a horse, pig or cow. Most preferably, the mammal is, however, a human.

The term "interleukin 10 (IL-10)" as used herein refers to a cytokine having strong anti-inflammatory properties. It is also known as cytokine-synthesis inhibitory factor. IL-10 is secreted by monocytes and TH2 cells as well as regulatory T-cells. Its strong anti-inflammatory properties are based on its capability of eliciting a reduction of T-cell activation as well as a reduction of antigen presentation. IL-10 protects the organism from excessive inflammatory reactions. The structure of IL-10 of several species including rodents such as mice as well as humans is well known in the art. The human IL-10 polypeptide forms a homodimer. Each subunit is 178 amino acids long. The gene for IL 1 is located on chromosome 1 (Eskdale 1997, Immunogenetics 46(2): 120-8; Zdanov 1995, Structure 3(6): 591-601). For example, the Accession number NM_010548.2 shows the corresponding sequences of murine IL-10, whereas the Accession number depicted in NM_000572.2 or P22301 shows the corresponding sequences of human IL-10.

It will be understood that the present invention also encompasses variants of the aforementioned specific IL-10 polypeptides. Such variants may be chemically modified or genetically engineered variants having essentially the same anti-inflammatory properties as the aforementioned IL-10 polypeptides. Moreover, variants may be homologous or orthologous polypeptides from other species. Preferably, such variants have an amino acid sequence being at least 40%, at least 50%, at least 60%, at least 70%, at least 75%, at least 80%, at least 85%, at least 90%, at least 95%, at least 98% or at least 99% identical to the amino acid sequence of the specif. The term "identical" as used herein refers to sec aforementioned IL-10 polypeptides. Sequence identity characterized by determining the number of identical amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215: 403). The percent identity values are, preferably, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5: 151) or the programs Gap and BestFit (Needleman 1970, J Mol Biol 48: 443; Smith 1981, Adv Appl Math 2: 482), which are part of the GCG software packet (Genetics Computer Group 1991, 575 Science Drive, Madison, Wis., USA 53711), may be used. It will be understood that these variants shall also have essentially the same anti-inflammatory properties as the aforementioned IL-10 polypeptides.

The IL-10 polypeptide is transcribed in accordance with the present invention from an mRNA molecule which has been transfected into the macrophage. The nucleotide sequence for such an mRNA molecule or the nucleotide sequence for a DNA molecule encoding it can be established by the skilled artisan without further ado for a given polypeptide such as the IL-10. The mRNA to be transfected can be chemically synthesized or can be obtained from a DNA template by in vitro transcription. Suitable techniques are well known in the art and commercial kits for carrying out such in vitro transcription reactions are available. Nucleotide sequences for IL-10 encoding mRNA or DNA are well known in the art and are, preferably, described by such nucleotide sequences can also be applied for deriving a suitable nucleotide sequence for the IL-10 encoding mRNA to be applied in accordance with the present invention. Preferably, the mRNA to be transfected into the macrophage in accordance with the present invention differs from naturally occurring mRNA in the poly-A-tail and/or the cap-structure at the 5' rend of the mRNA molecule, i.e. it is an artificial mRNA differing in its composition from the endogenously transcribed mRNA encoding IL-10. Moreover, nucleotide analogs can be used for the synthesis of the mRNA. Various nucleotide analogs have been reported to increase the stability of a mRNA. More preferably, the poly-A tail and/or cap-structure of the artificial mRNA which is transfected into the macrophage confers increased stability to the mRNA molecule. The mRNA to be transfected can be homologous or heterologous with respect to the macrophage, i.e. the mRNA and the macrophage may be from the same species or may be from different species.

The macrophage to be applied in the composition according to the present invention shall be transfected with mRNA encoding IL-10. The mRNA for the IL-10 is, thus, exogenously supplied to the macrophage rather than being transcribed from its endogenous IL-10 gene. Techniques for introducing mRNA into a cell such as a macrophage are well known in the art. A cell may be transfected with mRNA by physical techniques such as micro-injection of the mRNA or may be transfected by electroporation based methods such as nucleofection (see Pascal 2005, J Neurosci Methods 142(1): 137-43; Aluigi 2006, Stem Cells, 24(2): 454-461 Maasho 2004, Journal of Immunological Methods, 284(1-2): 133-40; WO 2007/090647). For the nucleofection technique, commercial kits are available (e.g., from Lonza Cologne GmbH). The transfected mRNA encoding IL-10 will be translated into the IL-10 polypeptide upon transfection into the macrophage.

By "overexpressing" it is meant that the IL-10 polypeptide is produced in the transfected macrophage compared to a non-transfected macrophage in a statistically significant higher amount. Whether an amount of IL-10 produced by the macrophage is significantly higher can be determined by standard statistically techniques. Preferably, the transfected macrophage in the composition to be applied according to the present invention expresses IL-10 at least 2-fold, at least 4-fold, at least 6-fold or at least 7-fold higher than a macrophage which has not been transfected by the IL-10 encoding mRNA. The person skilled in the art can determine an amount of mRNA which results in such an overexpression without further ado. Suitable amounts of mRNA are, preferably, within the range of 3 to 9 μg RNA for between $1 \times 10^6$ to $5 \times 10^6$ macrophages.

Thus, the macrophage referred to in accordance with the composition of the present invention is, preferably, obtained by a method comprising the steps of:
  (a) obtaining a macrophage from a sample of a subject; and
  (b) transfecting mRNA encoding IL-10 into said macrophage.

The macrophage can be obtained from a tissue sample of a subject, preferably, the subject to be treated by the composition. The tissue sample is, preferably, a peritoneal sample. The macrophage is, preferably, obtained from the sample by affinity purification based on the CD11b marker protein present on the macrophages, well known in the art. The corresponding Accession numbers of the murine CD11b and the human CD11b sequences are shown, e.g., in NM_008401.2 and NM_000632.3 or P11215, respectively. However, the techniques for isolating macrophages referred to elsewhere herein can be also applied. The isolated macrophages are, subsequently, transfected with mRNA encoding IL-10 in an amount resulting in the production of a therapeutically effective dose of IL-10 upon translation into IL-10 polypeptide. Details are also described elsewhere herein. The transfected macrophages can then be formulated in a suitable composition and applied as a medicament.

Moreover, it will be understood that the macrophages according to the present invention are, preferably, cultivated upon transfection for a time and under conditions sufficient for allowing effective translation of the mRNA into IL-10 polypeptide before the composition is formulated. Moreover, it is to be understood that only viable macrophages should be used for the composition of the present invention. Accordingly, prior to formulation as a composition of the present invention, the macrophages are, preferably, cultivated for at least 3 hours, at least 4 hours, at least 5 hours or at least 6 hours after transfection. Moreover, the non-viable macrophages shall be removed prior to formulation of the composition according to the present invention. More preferably, the composition is formulated and the medicament is to be applied between 6 to 72 hours, more preferably, between 6 and 24 hours and, most preferably, at about 6 hours after transfection.

The aforementioned macrophage is applied according to the present invention in a composition. Such a composition, in accordance with the present invention, comprises additional compounds, preferably, a pharmaceutically acceptable carrier. The pharmaceutically acceptable carrier must be acceptable in the sense of being compatible with the macrophage and other ingredients of the composition and being not deleterious to the recipient thereof. The said carrier may be a gel or a liquid. Examples of liquid carriers are phosphate buffered saline solution, water, physiological saline, Ringer's solutions, and the like. Suitable carriers comprise those mentioned above and others well known in the art, see, e.g., Remington's Pharmaceutical Sciences, Mack Publishing Company, Easton, Pa. Preferably, the pharmaceutically acceptable carrier is a physiological buffer or medium in which the macrophage is maintained and/or can be applied to a subject to be treated in accordance with the invention. Moreover, the composition may comprise additional drugs which improve or facilitate the anti-inflammatory effect of the IL-10 overexpressing macrophage. Preferably, a further drug to be included into the composition according to the present invention is TGF-β well known in the art. The TGF-β can be TGF-β1, TGF-β2 or TGF-β3. The corresponding sequences of murine and human TGF-β1 are shown, e.g., in Accession number NM_011577.1 and NM_000660.4 or P01137, respectively. The corresponding sequences of human TGF-β2 are shown, e.g., in Accession number NM_0011355599.2

The composition referred to herein above shall be used as a medicament. The term "medicament" as used herein refers to a pharmaceutical composition comprising the macrophage described above as pharmaceutical active compound. The medicament is, preferably, administered in a therapeutically effective dose. A therapeutically effective dose refers to an amount of the macrophage to be used in the composition applied according to the invention which prevents, ameliorates or treats the symptoms accompanying a disease or disorder referred to in this specification. Therapeutic efficacy and toxicity of a given drug including the cell based therapeutic according to the present invention can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Dosage recommendations shall be indicated in the prescribers or users instructions in order to anticipate dose adjustments depending on the considered recipient.

The medicament in accordance with the present invention is, preferably, suitable for topical as well as systemic applications. It can be administered at least once in order to treat or ameliorate or prevent a disease or condition recited in this specification. However, the medicament can also be administered more than one time.

The medicament referred to in this specification may be used for human or non-human therapy of various diseases or disorders. Preferably, said medicament is used for treating and/or preventing inflammation or a disease or disorder associated therewith. More preferably, the medicament is used for the treatment and/or prevention of a disease or disorder selected from the group consisting of myocarditis, autoimmune diseases, rheumatoid disease, rheumatoid arthritis, and multiple sclerosis. Most preferably, the medicament is for the treatment and/or prevention of myocarditis.

The symptoms accompanying the aforementioned diseases and disorders are well known to those skilled in the art and are described in standard text books of medicine.

Advantageously, it has been found in the studies underlying the present invention that macrophages which are transfected with mRNA encoding the anti-inflammatory cytokine IL-10 can be used for treating and/or preventing inflammatory diseases or disorders such as myocarditis. Specifically, it was found that murine macrophages from peritoneal tissue which have been transfected with an effective amount of IL-10 encoding mRNA efficiently inflammatory processes in a mouse myocarditis model (see Examples below). Adverse side effects which had been reported previously for macrophages transfected with DNA plasmids or viral vectors did not occur. Moreover, the transfection of mRNA is a highly efficient process which basically complies with the GMP provisions for human application.

In addition, the inventors were able to demonstrate beneficial effects after injection of IL-10 overexpressing macrophages both in a prophylactic and therapeutic approach: In the first clinical setting of macrophage application, autoimmune myocarditis was induced by subcutaneous injection of troponin I. IL-10 overexpressing macrophages were injected on day 14, 21 and 28 when autoimmune myocarditis was completely developed. This setting represents a therapeutic approach as the genetically modified macrophages were injected after myocarditis became clinically apparent. In the second clinical setting, IL-10 overexpressing macrophages were injected simultaneously with troponin I immunization on day 0, 7 and 14. Here a prophylactic approach is displayed, that should prevent development of autoimmune myocarditis before clinical symptoms became evident.

The present invention, in principle, contemplates, thus, a method for treating and/or preventing inflammation or a disease or disorder associated therewith in a subject suffering therefrom comprising the steps of:
(a) obtaining a macrophage from said subject;
(b) transfecting mRNA encoding IL-10 into said macrophage;
(c) formulating said macrophage in a composition suitable for administration to the said subject; and
(d) administering said composition to the subject in a therapeutically effective dosage.

In a preferred embodiment of the composition for use as a medicament according to the present invention, said composition is for application in the subject from which the macrophage was derived. Accordingly, an autologous cell therapy is envisaged, i.e. the donor subject and the acceptor subject of the macrophage is identical.

In a preferred embodiment of the composition for use as a medicament according to the present invention, said macrophage further expresses a polypeptide which facilitates the anti-inflammatory properties of the macrophage comprised by the composition of the invention. Preferably, said polypeptide is TGF-β.

In a preferred embodiment of the composition for use as a medicament according to the present invention, said macrophage comprised by the composition of the invention further expresses a polypeptide which facilitates migration of the macrophage to a target tissue in an organism. Preferably, said polypeptide is a chemokine-receptor and, more preferably, CXCR-4 and/or CCR-2. The corresponding murine CXCR-4 sequences are shown, e.g., in Accession number NM_009911.3. The corresponding human CXCR-4 sequences are shown, e.g., in Accession number NM_001008540.1 or P61073.1. The corresponding sequences of murine CCR-2 are shown, e.g., in NM_009915.2. The corresponding sequences of human CCR-2 are shown, e.g., in NM_001123041.2 or P41597.1. These chemokine-receptors are particularly useful for attracting the macrophage to the myocarditis in the heart.

The present invention also relates to a method for manufacturing a medicament for treating and/or preventing inflammation or a disease or disorder associated therewith comprising the steps of:
(a) obtaining a macrophage from a sample of said subject;
(b) transfecting mRNA encoding IL-10 into said macrophage; and
(c) formulating said macrophage in a composition suitable for administration to the said subject, whereby the medicament is manufactured.

Details on how to obtain and transfect the macrophage and on how to formulate the macrophage as a composition for the use as a medicament can be found elsewhere in this specification. It will be understood that the aforementioned method is carried out according to GMP standards.

In a preferred embodiment of the method of the invention, said medicament is for the treatment and/or prevention of a disease or disorder selected from the group consisting of: myocarditis, autoimmune diseases, rheumatoid disease, rheumatoid arthritis, and multiple sclerosis.

In another preferred embodiment of the method of the invention, said macrophage expresses IL-10 at least 2-fold, at least 4-fold, at least 6-fold or at least 7-fold higher than a macrophage which has not been transfected by the IL-10 encoding mRNA.

Finally, the present invention also contemplates a kit for manufacturing a medicament for treating and/or preventing inflammation or a disease or disorder associated therewith comprising (a) a device for isolating macrophages from a sample of a subject;
(b) a transfection reagent for mRNA; and
(c) (i) mRNA encoding IL-10 or (ii) a polynucleotide encoding IL-10 together with reagents for transcription thereof.

The term "kit" as used herein refers to a collection of the aforementioned components, preferably, provided in separately or within a single container. The container also comprises instructions for carrying out the method of the present invention. These instructions may be in the form of a manual or may be provided by on a data storage medium or device such as an optical storage medium (e.g., a Compact Disc).

Devices and reagents referred to in accordance with the kit of the invention have been further specified elsewhere herein and are also well known to the person skilled in the art.

All references cited in this specification are herewith incorporated by reference with respect to their entire disclosure content and the disclosure content specifically mentioned in this specification.

FIGURES

FIG. 1: mRNA-nucleofection of different macrophage populations

Two different populations of macrophages were compared for overexpression of EGFP (Enhanced Green Fluorescent Protein): lienal vs. peritoneal macrophages. Respectively, 3 µg mRNA were transfected and EGFP expression was measured 24 h later by FACS analysis. MOCK transfected cells and EGFP nucleofected cells were compared. Top row: peritoneal macrophages; bottom row: lienal macrophages. EGFP expression was significantly higher and more reproducible in peritoneal than in lienal macrophages. In this representative experiment, 40% EGFP positive lienal macrophages and 80% EGFP positive peritoneal macrophages were detected.

Figure 2:
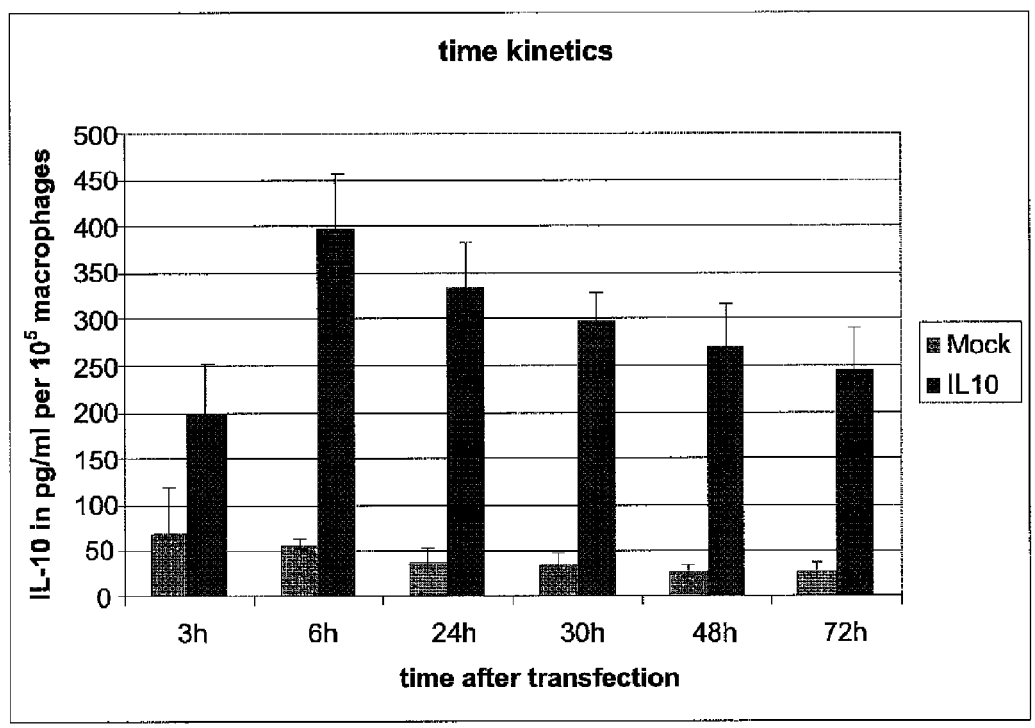

FIG. 2: Interleukin-10 ELISA—time kinetics

IL-10 levels were analyzed in vitro in the supernatant of macrophages 3, 6, 24, 30, 48 and 72 h after nucleofection of 3 µg mRNA for IL-10. MOCK transfected macrophages were used as a negative control. 6 h after mRNA-nucleofection, the maximum IL-10 concentration could be detected. Per $10^5$ macrophages in the positive group, 399±59 pg/ml IL-10 and in the negative group, 57±6 pg/ml IL-10 could be detected. In the negative control, MOCK transfection resulted in a marginal increase of IL-10 levels right after the nucleofection procedure. Within 24 h, IL-10 levels decreased to baseline values again. Mean values of three independent experiments are depicted.

Figure 3:
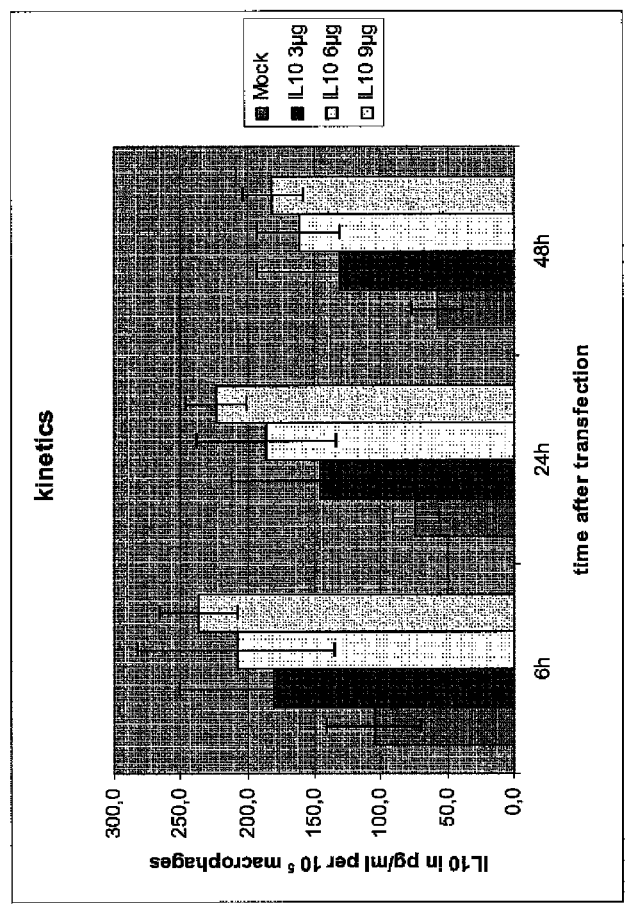

FIG. 3: Interleukin-10 ELISA—concentrations

In vitro the IL-10 concentration in the supernatant of macrophages was analyzed 6, 24 and 48 h after nucleofection of 3, 6 and 9 µg mRNA. A significant increase in IL-10 production could be detected when nucleofection was performed with raising amounts of mRNA. This observation could be confirmed at all time points. Mean values of four independent experiments are depicted.

FIG. 4: Morphological tracking of injected macrophages by Red Fluorescent Protein (RFP)

In one group, myocarditis was induced by immunization with troponin I as described earlier (Göser 2006, Circulation 114: 1693-1702). RFP$^+$ macrophages overexpressing IL-10 were injected intravenously. Healthy A/J wildtype mice, who did not receive any macrophages served as a negative control. One week after injection, the recipient mice were sacrificed and heart, lung, kidney, liver, spleen, skin and lymph nodes were analyzed for RFP$^+$ macrophages to detect distribution of the cells within the host body. No RFP-positive macrophages could be detected within the lungs, kidney, skin, liver and muscle. In the spleen and lymph nodes a weak red background staining—similar to RFP—could be detected, but no differences were seen between the positive and control mice. Significantly more RFP$^+$ macrophages could be detected within the heart compared with the control mouse. These findings may indicate a targeted therapy to sites of inflammation.

Figure 5:
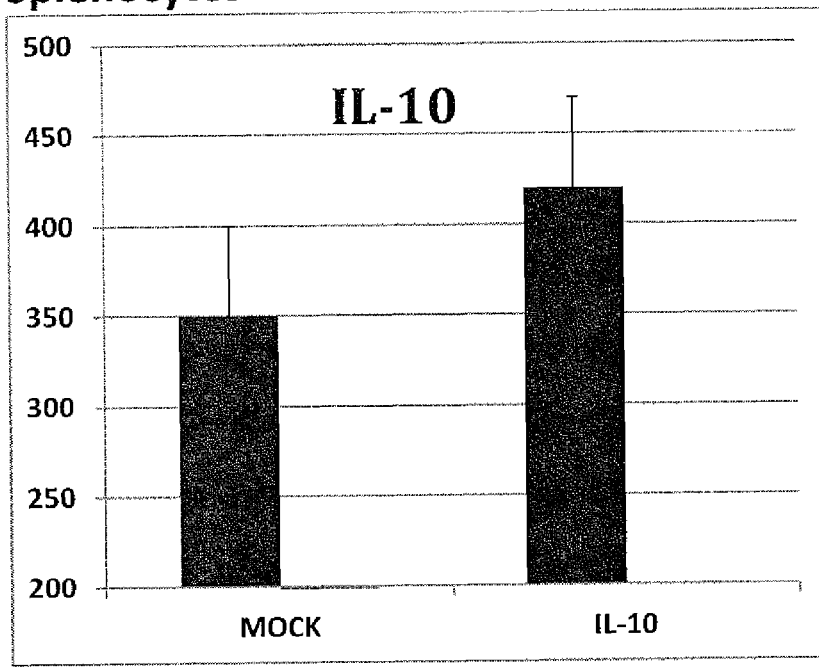
Figure 5:
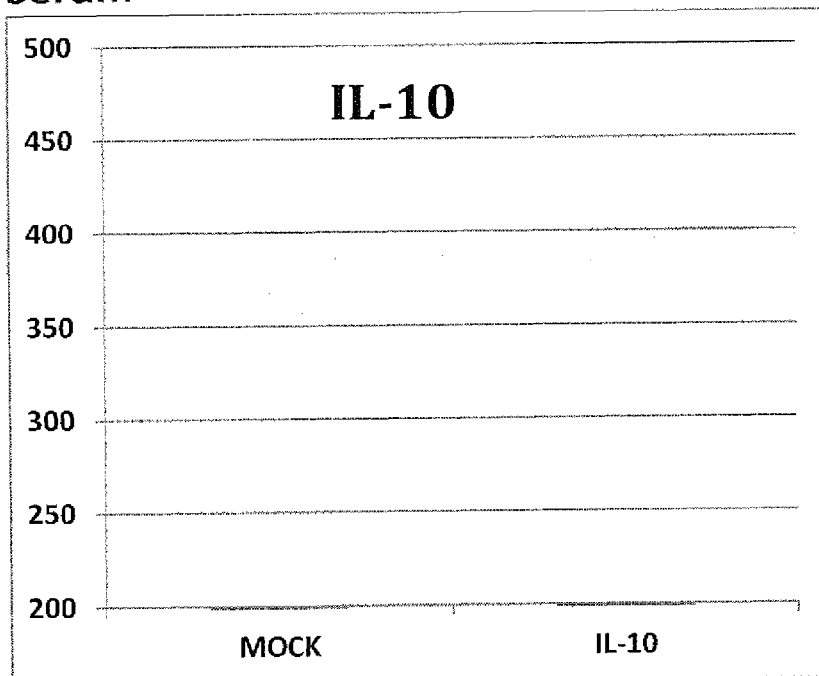

FIG. 5: Functional tracking of injected macrophages by IL-10 production

Top: In healthy A/J WT mice, i.e. mice without induction of myocarditis, IL-10 overexpressing macrophages were administered. MOCK transfected macrophages represented the negative control. After 24 h, the spleen was extracted and homogenized. The IL-10 concentration was measured in the supernatant of the splenocytes by ELISA. The inventors could detect a basal IL-10 production in splenocytes of WT A/J mice after administration of MOCK transfected macrophages, but significantly more IL-10 was produced in splenocytes after IL-10 overexpressing macrophages were injected. Again this could indicate a targeted therapy as macrophages seem to home back to organs of the mononuclear phagocyte system when inflammation is missing.

Bottom: IL-10 levels were determined in the blood serum of the above MOCK and IL-10 nucleofected A/J WT mice. $10^6$ macrophages were transfected respectively and 24 h later IL-10 levels were determined in the serum by ELISA. Neither in MOCK nor in IL-10 transfected mice relevant IL-10 concentrations were detectable. Once more this finding could indicate a targeted therapy with no/low systemic side effects.

Figure 6:
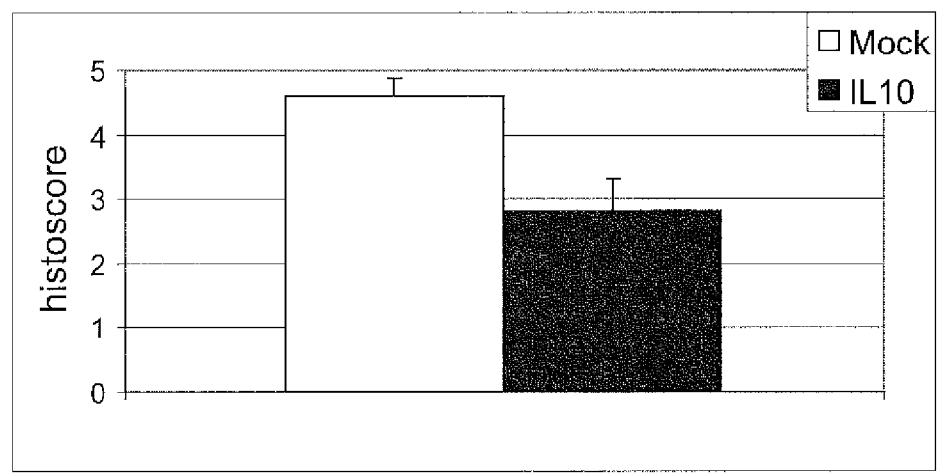

FIG. 6: Histological analysis of myocardial inflammation

Determination of the Histo-Score: myocardial sections were paraffin embedded and inflammation was quantified by H&E staining. A graduation of infiltrating cells was made 20%-wise (grade 1 to 5). After induction of myocarditis IL-10 overexpressing macrophages were injected on day 0, 7 and 14. On day 21 animals were sacrificed and histological analysis was performed. MOCK transfected macrophages represented the control group. Overall myocardial inflammation was significantly decreased after treatment with IL-10 overexpressing macrophages compared with controls. In this representative experiment, the mean Histo-Score was 2.2±0.6 for IL-10 treated mice vs. 3.5±0.5 for the MOCK control (p=0.024).

FIG. 7: Immunohistochemical staining in myocardial inflammation a) A detailed subanalysis of inflammatory cells was performed in myocardial sections. CD3$^+$ lymphocytes, CD68$^+$ macrophages and IL-10 was analyzed after treatment with IL-10 and MOCK transfected macrophages. By trend more IL-10, less lymphocytes and less macrophages were detected in IL-10 treated mice compared with MOCK transfected animals. b) Additionally, overall infiltrating cells were analyzed by H&E staining which were reduced after IL-10 treatment (see also FIG. 6). Myocardial fibrosis was detected by Masson's-Trichrom staining. Again, a semiquantitative score (grade 1 to 5) was applied. No significant differences could be detected between both groups which could be a result of the early analysis right 21 days after the first induction of myocardial inflammation. Thus, it might be too early to detect relevant differences for myocardial fibrosis. Representative experiments are depicted.

Figure 8:
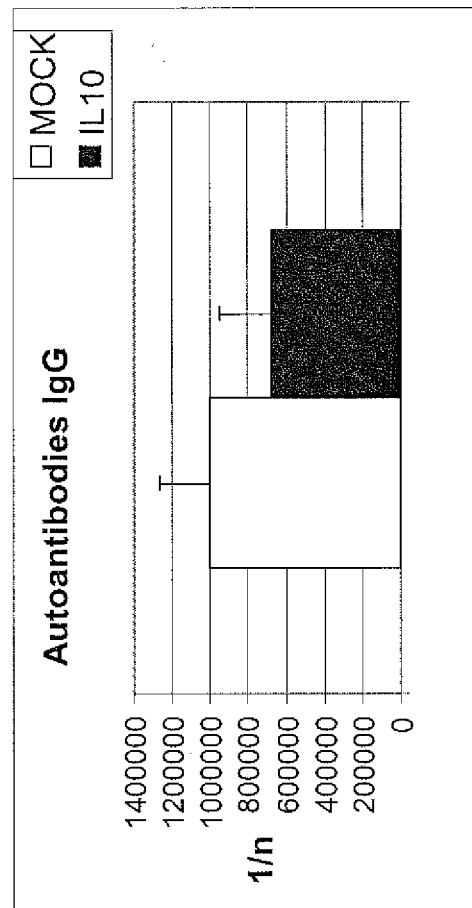

FIG. 8: Antibody titers

An enzyme-linked immunosorbent assay (ELISA) was established to measure the titer of autoantibodies against cTnI. Mice treated with intravenous application of IL-10 overexpressing macrophages showed significant lower titers of autoantibodies compared to mice treated with MOCK transfected macrophages; see Example 1.7.

Figure 9:
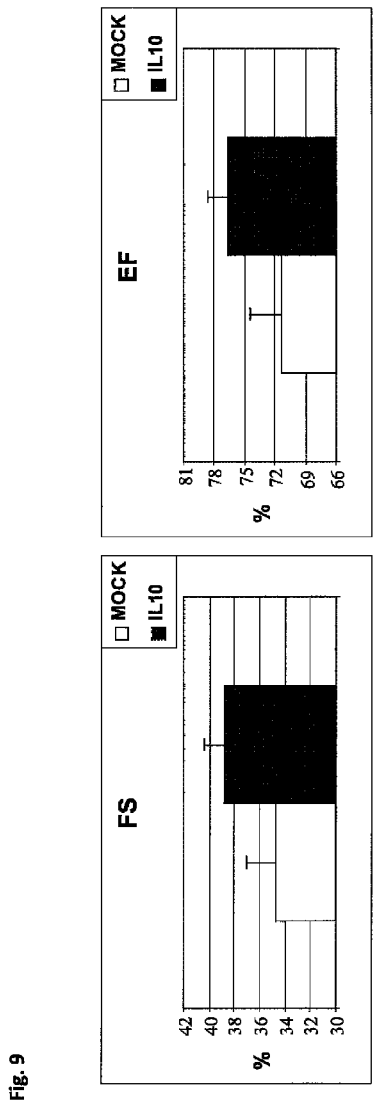

FIG. 9: Functional analysis of heart failure by echocardiography

Echocardiography was performed on day 21 after induction of myocarditis in IL-10 and MOCK treated mice. The ejection fraction (EF) and the fractional shortening (FS) were not significantly different between both groups, but by trend a better left ventricular function was detected for IL-10 treated heart failure mice (p=0.156 respectively).

FIG. 10: Physical performance in the running wheel

Mice were treated with IL-10 overexpressing macrophages and compared with a MOCK transfected control group as described above. Between day 14 and 21, i.e. within the third week, the inventors analyzed the walking time and distance the mice performed voluntarily in the running wheel. The inventors could detect a better physical performance as walking distance and time spent in the wheel were significantly higher in IL-10 treated animals compared with the MOCK group. Total exercise time (p=0.055), average exercise time per day (p=0.043), total walking distance (p=0.046) and average walking distance per day (p=0.020) were compared with MOCK transfected control mice.

EXAMPLES

The invention will be merely illustrated by the following Examples. The said Examples shall, whatsoever, not be construed in a manner limiting the scope of the invention.

Example 1

Materials and Methods 1.1 Isolation, Characterization and Culture of Murine Macrophages A/J mice (Jackson Lab; USA) older than 8 weeks served as donors for macrophage isolation. After cervical dislocation, 15 ml of a Hanks Balanced Salt Solution (HBSS; Gibco, USA) were injected intraperitoneally. HBSS contained 10% HBSS, 1% HEPES and 2% FCS (fetal calf serum). After 5 minutes of incubation, the buffer was aspirated with a syringe and the cell suspension was centrifugated at 300 g. Then the pellet was resuspended in 450 μl PBS with 0.3% BSA (bovine serum albumine) and 2 mM EDTA. 50 μl of magnetically labeled human anti-mouse CD11b antibody (Miltenyi Biotec, Germany) was added for 20 minutes. CD11b positive monocytes/macrophages were extracted using a MS column (Miltenyi Biotec, Germany) according to manufacturers' instructions. Per mouse about 0.5×10$^6$ macrophages could be isolated. Macrophages of two mice were pooled to obtain one million cells for subsequent mRNA-nucleofection.

Additionally murine macrophages were isolated from the spleen. The spleen was extracted, cut into small pieces and homogenized by squeezing the cells through a 30 μm pre-separation-filter (Miltenyi Biotec, Germany). Afterwards, CD11b positive monocytes/macrophages were purified as described above.

1.2. Preparation of RFP$^+$ Macrophages

For in vivo tracking of administered macrophages, cells were isolated from RFP$^+$-transgenic mice. All cells of these mice express the Red Fluorescent Protein (RFP) which makes donor macrophages visible in the host. RFP$^+$-transgenic reporter mice were kindly provided by Prof H. J. Fehling (Institute for Immunology, Ulm University, Luche 2007 Eur J Immunol 37: 43-53). To avoid cell rejection, the RFP$^+$ C57BL/6-inbred reporter mice were backcrossed with A/J mice. To confirm and accelerate the backcross procedure, a genome scanning (Jackson Lab, USA) was performed to identify the mice with the most autologous genotype. Thus, a specific backcross to the A/J background was possible.

1.3 Vector Construction and In Vitro Transcription

The murine 537 bp IL-10 gene (Accession Number NM_010548) was cloned into the pBluescript II SK(+) vector and purchased from Eurofins (France). For the experiments, the IL-10 plasmid was diluted 1:10 and cloned into a pcDNA3.1/V5-His TOPO vector (Invitrogen, USA). The plasmid was enzymatically linearized using SeaI and in vitro transcription was performed as described earlier (Wiehe 2006 Regen Med 1: 223-234; Wiehe 2007 J Cell Mol Med 11: 521-530).

1.4 mRNA-Nucleofection of IL-10 and EGFP $10^6$ macrophages were dissolved in 100 µl mouse macrophage Nucleofector® kit (AMAXA, Germany) and 3 µg of IL-10 mRNA were added. For nucleofection, program X-01 of the Nucleofector® device (AMAXA, Germany) was used. Afterwards macrophages were cultured in RPMI medium (PAA, Austria) containing 10% FCS and 1% PSG (penicillin-streptomycin-glutamine).

Alternatively, 3 µg of mRNA for Enhanced Green Fluorescent Protein (EGFP) were nucleofected. The DNA plasmid that served as a template for in vitro transcription was kindly provided by Dr. Peter Ponsaerts (University of Antwerp, Belgium). EGFP positive cells were detected by fluorescence activated cell sorting using a FACSDiva (Becton, Dickinson and Company, USA) as described in detail in Wiehe et al. (Wiehe 2007 J Cell Mol Med 11: 521-530).

1.5 Interleukin-10 ELISA a) Time-Dependent Effects of IL-10 Overexpression In Vitro $10^6$ macrophages were nucleofected with 3 µg mRNA for IL-10 as described above. Cells were seeded in 48 well plates and cultured for 3, 6, 24, 30, 48 and 72 h in 500 µl RPMI, 10% FCS and 1% PSG medium per well. The IL-10 concentration was determined in the supernatant using a DuoSet ELISA Development System (R&D Systems, USA). For detection, a Blue Star HRP Substrate (Diarect AG, Germany) was utilized. The ELISA was performed according to manufacturers' instructions.

b) Dose-Dependent Effects of IL-10 Overexpression In Vitro 3, 6 and 9 µg of mRNA for IL-10 were used for nucleofection. The IL-10 concentration in the supernatant was analyzed 6, 24 and 48 h later.

c) Determination of IL-10 Serum Level In Vivo

IL-10 levels were determined in the blood serum of healthy A/J mice after injection of MOCK and IL-10 nucleofected macrophages. No inflammation was induced in these mice. $10^6$ macrophages were transfected respectively and 24 h later IL-10 levels were determined in the serum by ELISA.

1.6 Murine Myocarditis Model a) Production and Purification of Cardiac Troponin I (cTnI)

Murine cTnI (Accession Number shown in P48787) was transformed into *E. coli* bacteria. The protein was expressed and purified by anion-cation-exchange as well as affinity chromatography. The quality of the extract was analyzed by SDS gel and Western Blot. A detailed protocol was provided earlier (Göser 2006, Circulation 114: 1693-1702; Göser 2005, Circulation 112: 3400-3407; Kaya 2002, J Immunol 168: 1552-1556).

b) Immunization

This procedure was described in detail earlier (Göser 2006, Circulation 114: 1693-1702; Göser 2005, Circulation 112: 3400-3407; Kaya 2002, J Immunol 168: 1552-1556). In brief, for induction of myocardial inflammation cTnI and complete Freud's adjuvant (CFA) were mixed in a 1:1 ratio. Afterwards an emulsion was generated. Female A/J mice at the age of 6 weeks were subcutaneously injected with 120 µg of the emulsion on day 0 and 7. A control group was immunized with an emulsion of the pre- and post-fraction from the cTnI and CFA alone.

c) In Vivo Application of Modified Macrophages

Effects of timing: i) IL-10 overexpressing macrophages were injected on day 0, 7 and 14 into the tail vein of A/J recipient mice. To confirm a sufficient mRNA-nucleofection, IL-10 levels were determined in vitro in the supernatant of macrophages as described above. This represents a prophylactic approach as therapy is initiated simultaneously with triggering of myocardial inflammation. Macrophages that underwent the nucleofection procedure without addition of IL-10 mRNA served as controls (i.e. MOCK transfection). ii) additionally macrophages were administered after myocarditis was clinically apparent on day 14, 21 and 28. This represents a therapeutic approach. Effects of the inflammatory setting: IL-10 overexpressing macrophages were intravenously injected into A/J mice with and without induction of myocarditis to analyze cell distribution.

1.7 Antibody Titers

An enzyme-linked immunosorbent assay (ELISA) was established to measure the titer of autoantibodies against cTnI. The 96-well plates were coated overnight at 48° C. with 5 mg/mL cTnI (100 mL/well) dissolved in bicarbonate buffer (0.1 M $NaHCO_3$/34 mM $Na_2CO_3$, pH 9.5). 1×PBS/0.05% Tween 20 served as washing buffer. Plates were then coated with 1% Gelatine (Cold Water Fish, Sigma, 300 mL/well). After an incubation period of 2 h at 37° C. and rinsing, IgG (Sigma A2554) diluted to 1:5000 was applied for detection (1 h at room temperature, 100 mg/well). Dilution series of serum samples were performed as follows: 1:100, 1:400, 1:1600, 1:6400, and 1:25 600. Blue Star HRP substrate solution (Diarect) was then applied for 30 mM at room temperature (100 mL/well) and the colour reaction was stopped with 0.3 M $H_2SO_4$. All samples were measured in duplicate. Optical densities of each well were determined using a microplate reader set to 450 nm. The antibody endpoint titer of each mouse was determined as the highest positive dilution of antibody; see FIG. 8 for result.

1.8 Functional Analysis of Heart Failure a) Transthoracic Echocardiography

Echocardiography was performed using an ATL-HDI 9000 (Philips, The Netherlands) device with a 10 MHz linear transducer. In the longitudinal axis enddiastolic and endsystolic diameter, ejection fraction (EF), fractional shortening (FS) and heart rate were determined. Mice were investigated after anaesthesia with 1-2% (v/v) isoflurane.

b) Treadmill Exercise Test

A running wheel was placed in each cage and every mouse had its own device. The individual voluntary walking distance and time was measured. After one week of adaption the parameters obtained in the third week after application of IL-10 overexpressing macrophages were analyzed.

1.9 Histological Analysis a) Determination of the Histo-Score

Serial cross-sections of 5 mm thickness each through the entire heart were prepared and stained with haematoxylin and eosin (H&E) in order to define the level of inflammation. Masson's trichrome staining was used to determine the extent of collagen deposition. An independent examiner blinded to the treatment arm of the respective specimens explored every fifth cross-section and classified them according to the six-tier scoring system published previously (Kaya 2002, J Immunol 168: 1552-1556; Göser 2006, Circulation 114:1693-702; Kaya 2008, Circulation 118: 2063-72).

b) Determination of Myocardial Fibrosis

Myocardial fibrosis was semi-quantitatively analyzed by Masson's-Trichrom staining according to the pattern above (Kaya 2002, J Immunol 168: 1552-1556; Göser 2006, Circulation 114: 1693-702; Kaya 2008, Circulation 118: 2063-72).

c) Immunohistochemical Analysis of Myocardial Inflammation

Myocardial inflammation was assessed by immunohistochemistry as described earlier (Zimmermann 2005, Int J Cardiol 104: 92-100). In brief, CD3 positive lymphocytes, CD68 positive macrophages and IL-10 were detected within the myocardium by the avidin-biotin-peroxidase complex. Myocardial sections were fixed with formalin and incubated with 0.1% proteinase (Sigma, USA) for 10 minutes. A 1% $H_2O_2$/methanol solution was used to block endosomal peroxidase activity. Unspecific antigens were blocked with rabbit or goat serum in a 1:10 dilution. A polyclonal rat anti-mouse CD68 antibody (dilution 1:50; clone FA-11, Acris Antibody GmbH, Germany), a polyclonal goat anti-mouse CD3 antibody (dilution 1:50; Santa Cruz, USA) and a polyclonal goat anti-mouse IL-10 M-18 antibody (dilution 1:100; Santa Cruz, USA) were used as a primary antibody. A biotinylated rabbit anti-goat (Dako, Germany) and goat anti-rat antibody (BioLegend, USA) was diluted 1:200 and served as a secondary antibody, respectively. Myocardial sections were analyzed every 25 µm for each antigen using an Axioskop 2 plus microscope (Zeiss, Germany). Thus, at least 20 sections were available which represent about 400 high power fields (i.e. 40-fold magnification). A semiquantitative score system was applied for IL-10. Staining intensity was indicated from 0 (i.e. no IL-10 detection) to "+++" (i.e. strong IL-10 detection). CD3 and CD68 positive cells were counted under the light microscope (cells/mm$^2$). Immunohistochemical analysis was performed blinded by experienced investigators.

1.10 Statistical Analysis

Data were analyzed with the Kruskal-Wallis test followed by the Mann-Whitney U test to explore the significance between treatment groups. $P<0.05$ was considered significant. The statistical software SPSS (version 15.0) was used for all calculations.

Example 2

Results 2.1 mRNA-Nucleofection of Different Macrophage Populations

To establish an optimized protocol for mRNA-nucleofection, two different populations of macrophages were compared for overexpression of EGFP: lienal vs. peritoneal macrophages. Respectively, 3 µg mRNA were transfected and EGFP expression was measured 24 h later by FACS analysis. A significantly higher expression of EGFP could be observed in peritoneal than in lienal macrophages (FIG. 1). On average, 20% (1-40%) EGFP positive lienal macrophages and 82% (80-85%) EGFP positive peritoneal macrophages could be detected. Furthermore, isolation of macrophages from the abdominal cavity is faster, easier and more reproducible compared with the isolation of lienal macrophages. Thus, peritoneal macrophages were isolated for this study.

2.2 Interleukin-10 ELISA a) Time-Dependent Effects of IL-10 Overexpression In Vitro After nucleofection of macrophages with 3 µg mRNA for IL-10, IL-10 levels in the supernatant were analyzed 3, 6, 24, 30, 48 and 72 h later. MOCK transfected macrophages were used as a negative control. 6 h after mRNA-nucleofection, the maximum IL-10 concentration could be detected which represents a 7-fold increase compared with the negative control. Per $10^5$ macrophages in the positive group, 399±59 pg/ml IL-10 and in the negative group, 57±6 pg/ml IL-10 could be detected. As mRNA-nucleofection represents a transient form of genetic cell modification IL-10 level constantly decreased within a couple of days. In the negative control, MOCK transfection resulted in a marginal increase of IL-10 levels right after the nucleofection procedure. Within 24 h IL-10 levels decreased to baseline values again. Additionally, the supernatant of the macrophages has been removed regularly to analyze different intervals of IL-10 production. Transfected macrophages produced nearly all IL-10 within the first 24 hours (data not shown). FIG. 2 shows the mean IL-10 concentrations (pg/ml per $10^5$ macrophages) of three independent experiments.

b) Dose-Dependent Effects of IL-10 Overexpression In Vitro 3, 6 and 9 µg of mRNA for IL-10 were used for nucleofection. The IL-10 concentration in the supernatant was analyzed 6, 24 and 48 h later (pg/ml per $10^5$ macrophages). A significant increase of IL-10 could be observed when nucleofection was performed with rising amounts of mRNA. This observation was confirmed at all time points investigated. Also the above described time kinetics could be confirmed in this experiment. Median values from four independent experiments are depicted in FIG. 3.

2.3 Targeted Therapy Using IL-10 Overexpressing Macrophages a) Tracking of Macrophages by Detection of RFP RFP$^+$ C57BL/6-inbred reporter mice were backcrossed with A/J mice. From these mice, RFP$^+$ macrophages were isolated. The injected macrophages could be tracked in WT mice by fluorescence microscopy and thus distinguished from innate macrophages. No relevant amounts of macrophages could be detected within the liver, skin, muscle, kidney, lungs, spleen and the lymph nodes. Significantly more RFP macrophages could be detected in the heart compared to the non-treated WT control mouse. These findings probably indicate a targeted therapy to sites of inflammation (FIG. 4).

b) Tracking of Macrophages by IL-10 Production

IL-10 overexpressing macrophages were injected intravenously into healthy A/J WT mice without induction of myocarditis. 24 h later the spleen was extracted, homogenized and IL-10 levels were determined by ELISA in the supernatant of the splenocytes. MOCK transfected macrophages served as a negative control. A significantly higher IL-10 production could be detected in the treatment group compared with the negative control. The mean IL-10 concentration was 350 vs. 420 pg/ml ($p<0.05$; FIG. 5, top). This result could indicate, that in healthy animals without any inflammation, IL-10 overexpressing macrophages leave the vasculature soon to be stored in the spleen. This represents a physiological pattern as macrophages usually home in organs of the macrophage monocytic phagocytic system (MMPS) if there is no active inflammation. Quiescent macrophages can be recruited from these tissues in the case of active inflammation.

c) Determination of IL-10 Serum Levels In Vivo

IL-10 levels were determined in the blood serum of MOCK and IL-10 nucleofected healthy WT A/J mice. $10^6$ macrophages were transfected respectively and 24 h later IL-10 levels were determined in the serum by ELISA. Neither in MOCK nor in IL-10 transfected mice a relevant IL-10 concentration was detectable; see FIG. 5, bottom. This observation indicates that there is no significant systemic increase in IL-10 levels and thus no relevant adverse side effects are expected.

2.4 Histological Analysis a) Determination of the Histo-Score

Figure 7A:
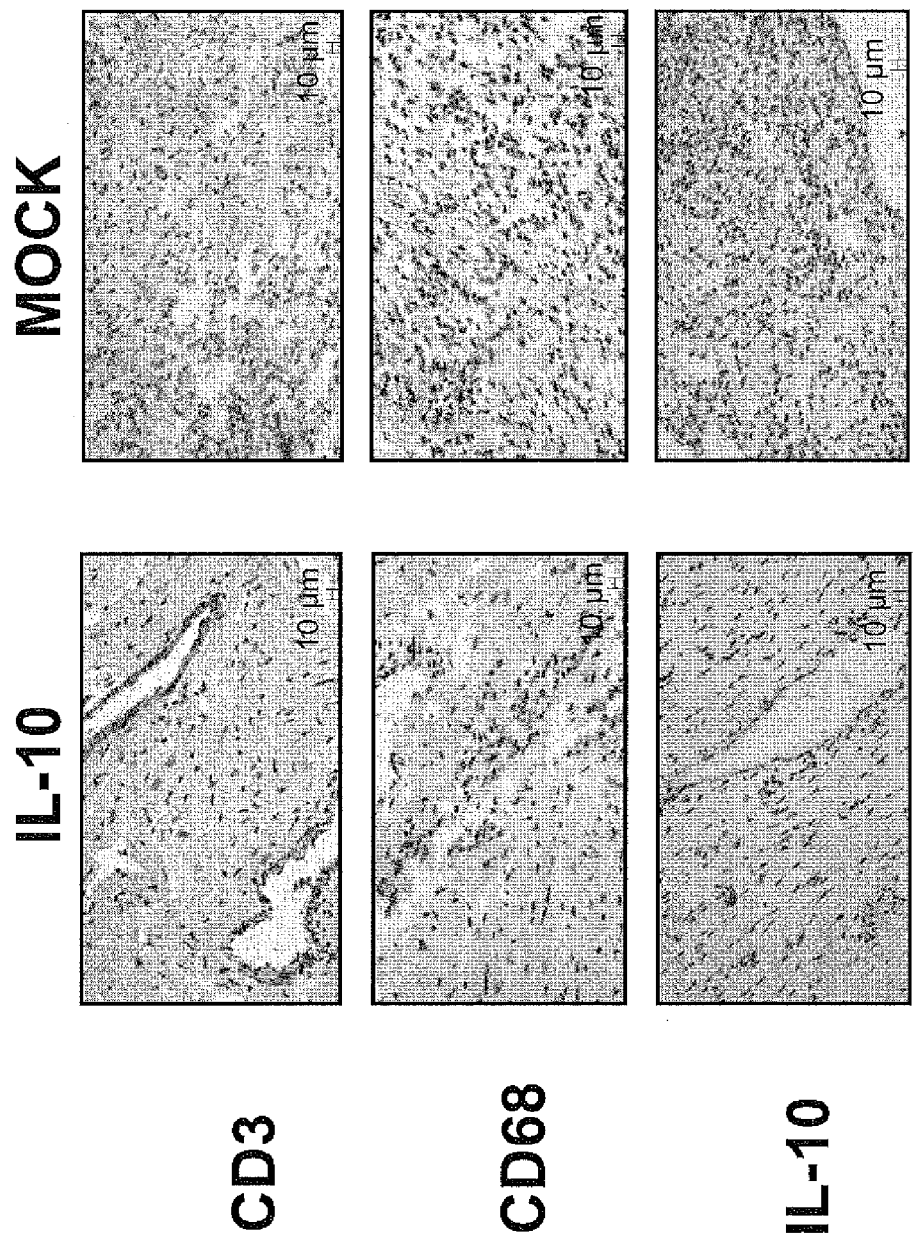

IL-10 was overexpressed in macrophages by nucleofection of 6 µg mRNA. $10^6$ macrophages were injected intravenously into A/J WT mice after induction of myocarditis. 21 days after first immunization the mice were sacrificed and H&E staining of myocardial sections was performed. MOCK transfected mice represented the negative control. Myocardial inflammation was analyzed by application of the Histo-Score. A significant reduction of infiltrating cells could be seen within the myocardium after application of IL-10 overexpressing macrophages (FIGS. 6 and 7a). The Histo-Score was 2.9±0.6 for IL-10 treated mice vs. 4.6±0.4 for the control group (p=0.004; FIG. 6).

b) Determination of Myocardial Fibrosis

Myocardial fibrosis was detected by Masson's-Trichrom staining. A semiquantitative score (grade 1 to 5) was applied in analogy to the Histo-Score. No significant differences could be detected between both groups which could be a result of the early analysis right 21 days after the first induction of myocardial inflammation. Thus, it might be too early to detect relevant differences for myocardial fibrosis. Representative experiments are depicted (FIG. 7b).

2.5 Antibody Titers

Three weeks after first immunization with cardiac troponin antibody titers against cardiac troponin was measured. Mice treated with intravenous application of IL-10 overexpressing macrophages showed significant lower titers of autoantibodies compared to mice treated with MOCK transfected macrophages (p<0.05; FIG. 8).

2.6 Functional Analysis of Heart Failure a) Transthoracic Echocardiography

Three weeks after first immunization with cardiac troponin, echocardiography was performed. MOCK transfected macrophages were injected as a control. By trend IL-10 treatment resulted in a better ejection fraction and fractional shortening than application of MOCK transfected macrophages. The fractional shortening (FS) was 38.8±1.4% in IL-10 treated mice and 34.6±2.0% in MOCK transfected animals (p=0.156). The ejection fraction (EF) was 77±2 in the IL-10 treated mice and 71±3 in the control group (p=0.156). A statistical significance was missed. FIG. 9 depicts a representative experiment. Each group consisted of 10 mice respectively.

b) Treadmill Exercise Test

Mice were treated as described above. During the third week after first immunization with troponin, voluntary physical performance was investigated using a running wheel. The time and distance was measured that mice acquired in the third week after intravenously injection of the genetically modified cells. Spontaneous physical activity was significantly increased after injection of IL-10 overexpressing macrophages. The mean walking distance per day was 5.6±0.7 km in the treatment group vs. 3.8±0.6 km in the control group (p=0.020; FIG. 10). Also total exercise time (p=0.055), mean exercise time per day (p=0.043) and total walking distance (p=0.046) were compared with MOCK transfected control mice.

2.7 Dose-Dependent Effects of IL-10 Therapy

The above experiments were carried out again, but this time only $5 \times 10^5$ genetically modified macrophages were injected intravenously. Now the inventors were not able to detect any significant differences for echocardiography and treadmill exercise tests between IL-10 overexpressing macrophages and the MOCK control. Also histological analysis could not detect any significant differences for myocardial CD3, CD68 and IL-10 distribution. Thus, a dose dependent efficacy of the therapeutic principle presented herein seems possible (data not shown).

Example 3

Discussion

In the present study, the inventors investigated an in vivo application of IL-10 overexpressing macrophages for anti-inflammatory therapy in a mouse model of autoimmune myocarditis. The inventors could demonstrate that myocardial inflammation could be reduced and clinical performance was increased after injection of genetically modified macrophages. Furthermore, the inventors gained evidence that their therapeutic approach displayed only a local action that was focused within the myocardium. There was no systemic impact of this therapy as the inventors could not detect elevated IL-10 plasma level after intravenous injection of IL-10 overexpressing macrophages. Significantly more RFP+ positive macrophages could be detected within the myocardium of Tn1 immunized mice in contrast to other tissues. Nearly no macrophages were seen in the liver, skin, muscle, lungs and the kidneys whereas an unspecific red background staining could be detected in the spleen and in lymph nodes. The inventors postulate that macrophages rather selectively migrate into the inflamed tissue, release IL-10 locally and thus mediate their anti-inflammatory effects specifically. Thus, in a clinical setting, adverse side effects could be reduced by this targeted therapy.

Finally, an in vivo application in patients with acute myocarditis seems basically possible as the nucleofection technique is adapted to the GMP-guidelines and the isolation of the macrophages can be arranged in an autologous setting (Wiehe 2006 Regen Med 1: 223-234; Wiehe 2007 J Cell Mol Med 11: 521-530). This fact is one major advantage of the therapy of the invention as earlier approaches were limited by the use of viral vectors, low efficacy and a potential procedural toxicity (El-Shemi 2004, Kidney Int 65: 1280-1289; Pinderski 2002, Circ Res 90: 1064-1071; Spight 2005, Am Physiol Lung Cell Mol Physiol 288: 251-265). As the inventors present a universal approach for a targeted anti-inflammatory therapy this method could be transferred to other processes characterized by local inflammation as Crohn's disease, vasculitis or rheumatoid arthritis. The inventors applied two clinical settings of macrophage application: i) autoimmune myocarditis was induced by subcutaneous injection of troponin I. IL-10 overexpressing macrophages were injected on day 14, 21 and 28 when autoimmune myocarditis was completely developed. This setting represents a therapeutic approach as the genetically modified macrophages were injected after myocarditis became clinically apparent. ii) IL-10 overexpressing macrophages were injected simultaneously with troponin I immunization on day 0, 7 and 14. Here a prophylactic approach is displayed, that should prevent development of autoimmune myocarditis before clinical symptoms became evident. In both settings, the inventors were able to demonstrate beneficial effects after injection of IL-10 overexpressing macrophages.

One challenge of the present study is the histological analysis of myocardial sections. Myocardial inflammation appears in clusters and so it is difficult to get an exact number of macrophages and lymphocytes as many cells may be located in the same area and cannot be distinguished separately. The inventors tried to solve this methodological limitation by analysis of at least 400 high power fields and calculation of the mean cell number per $mm^2$ for each antigen per heart. Within recent years there were numerous attempts to extent the standard heart failure therapy in myocarditis. Unspecific immunosuppressive therapy using prednisone, cyclosporine or azathioprine was introduced without convincing results (Mason 1995, N Engl J Med 333: 269-275). In viral dilated cardiomyopathy, a specific antiviral therapy with interferon β-1b was investigated. In a phase I study some beneficial effects could be detected for this therapy (Kühl 2003, Circulation 107: 2793-2798) but a phase II study and another clinical trial could not confirm the initial promising results (Schultheiss 2008, Circulation 118: 2312 (Abstract); Zimmermann 2010, J Card Fail 16: 348-356). Against this background, new anti-inflammatory therapies based on IL-10 overexpression seem worth to be further followed.

The anti-inflammatory power of the Th2-associated cytokine IL-10 has been utilized in a couple of recent studies. IL-10 mediates its immunomodulatory properties by inhibition of Th1 cells, macrophages and cytokines like NF-κB, TNF-α, IL-1 or IL-6 and thus protects the organism from overwhelming proinflammatory conditions (Matsumori 2001, Heart Fail Rev 6: 129-136). Recently, IL-10 was suggested as the effective part of some anti-inflammatory therapies as fenofibrate (Maruyama 2002, J Atheroscler Thromb 9: 87-92), quercetin—a flavonoid—(Milenkovic 2010, J Pharm Pharm Sci 13: 311-319), mesenchymal stem cells (Weil 2010, Surgery 148: 444-452), immunoglobulins (Matsumori 2010, Circ Res 106: 1533-1540) and methotrexate (Zhang 2009, Mediators Inflamm 2009: 389720). In contrast to these animal studies, patients with myocarditis showed a worse outcome when IL-10 serum levels were elevated (Fuse 2005, Eur J Heart Fail 7: 109-112; Nishii 2004, J Am Coll Cardiol 44: 1292-1297). This observation may be explained by the fact, that in fulminant myocarditis more pro-inflammatory cytokines are produced and consequently more IL-10 is released for counterbalancing. Nishio and colleagues administered recombinant IL-10 subcutaneously in a murine model of autoimmune myocarditis caused by the encephalomyocarditis virus (Nishio 1999, Circulation 100: 1102-1108). They could report a significantly higher survival rate in the treatment group compared with the control group. Furthermore myocardial lesions were smaller and the levels of TNF-α, IL-2 and iNOS in the heart were lower in IL-10 treated mice. Interestingly, the beneficial effects were only seen when IL-10 was begun on the day of virus inoculation (i.e. prophylaxis) whereas no effects were seen when IL-10 was administered later (i.e. therapy) (Nishio 1999, Circulation 100: 1102-1108). This observation could be confirmed in a murine model of fatal group B streptococcus sepsis (Nishio 1999, Circulation 100: 1102-1108). In a rat model of myocarditis, IL-10 was also protective when a plasmid vector expressing the IL-10 cDNA was transferred into the tibialis anterior muscle by electroporation (Palaniyandi 2004, Eur J Immunol 34: 3508-3515; Watanabe 2001, Circulation 104: 1098-1100). In contrast, in the present non-viral murine myocarditis model the inventors could detect beneficial effects of an IL-10 therapy in a prophylactic and in a therapeutic setting respectively.

In this study, the inventors report for the first time that application of IL-10 overexpressing macrophages could display beneficial effects in a murine model of autoimmune myocarditis. Recent attempts to introduce IL-10 therapy to a clinical setting were limited by the use of viral vectors, low efficacy and a potential procedural toxicity (El-Sheri 2004, Kidney Int 65: 1280-1289; Pinderski 2002, Circ Res 90: 1064-1071; Spight 2005, Am Physiol Lung Cell Mol Physiol 288: 251-265). The therapeutic approach of the present invention is adapted to the GMP-guidelines (Wiehe 2006, Regen Med 1: 223-234; Wiehe 2007, J Cell Mal Med 11: 521-530) and based on an autologous background. Thus, basically a bridge to a clinical application can be built. As nucleofection results in a transient overexpression of IL-10 there is no permanent genetic modification of the macrophages which furthermore supports a clinical use (Wiehe 2006, Regen Med 1: 223-234; Wiehe 2007, J Cell Mol Med 11: 521-530). Modifications of the mRNA could potentially influence the duration of IL-10 expression. Finally, the inventors present a first proof of principle for a new therapeutic approach in autoimmune myocarditis.

The invention claimed is:

1. A method for treating and/or reducing local inflammation in a subject, comprising the steps of:
    (a) obtaining a macrophage from the subject;
    (b) transfecting mRNA encoding IL-10 into the macrophage, wherein said macrophage expresses IL-10;
    (c) formulating the macrophage in a composition suitable for administration to the subject; and
    (d) administering the composition to the subject in a therapeutically effective dosage, thereby treating and/or reducing the local inflammation in the subject, wherein the local inflammation is associated with myocarditis, autoimmune disease, rheumatoid disease, rheumatoid arthritis, or multiple sclerosis.

2. The method of claim 1, wherein the subject is human.

3. The method of claim 1, wherein the macrophage expresses IL-10 at least about 2-fold, at least about 4-fold, at least about 6-fold or at least about 7-fold higher than a macrophage which has not been transfected by the IL-10 encoding mRNA.

4. The method of claim 1, wherein the macrophage is a peritoneal macrophage.

5. The method of claim 1, wherein the composition is administered during or following development of the local inflammation.

6. The method of claim 1, wherein the subject exhibits clinical symptoms of the local inflammation.

7. The method of claim 1, wherein the composition is administered intravenously to the subject.

* * * * *